United States Patent
Power et al.

(10) Patent No.: US 12,097,103 B1
(45) Date of Patent: Sep. 24, 2024

(54) GARMENTS WITH FLUID RETENTION ASSEMBLIES AND RELATED METHODS

(71) Applicant: Knix Wear Inc., Toronto (CA)

(72) Inventors: Julie Power, Toronto (CA); Linda Kritikos, Toronto (CA); Christina Greco, Toronto (CA); Joanna Griffiths, Toronto (CA); Talia Greenberg, Toronto (CA); Jeremy Jiang, Kunshan (CN)

(73) Assignee: Knix Wear Inc., Toronto (CA)

( * ) Notice: Subject to any disclaimer, the term of this patent is extended or adjusted under 35 U.S.C. 154(b) by 0 days.

(21) Appl. No.: 18/327,716

(22) Filed: Jun. 1, 2023

(51) Int. Cl.
*A61F 13/496* (2006.01)
*A61F 13/15* (2006.01)

(52) U.S. Cl.
CPC ...... *A61F 13/496* (2013.01); *A61F 13/15268* (2013.01)

(58) Field of Classification Search
CPC .......... A61F 2013/530437; A61F 2013/53052; A61F 2013/53059; A61F 13/535; A61F 2013/53097; A61F 2013/5355; A61F 2013/53445
See application file for complete search history.

(56) References Cited

U.S. PATENT DOCUMENTS

| | | | |
|---|---|---|---|
| 2,985,170 | A | 5/1961 | Title |
| 3,489,149 | A | 1/1970 | Larson |
| 3,608,551 | A | 9/1971 | Seijo |
| 3,687,141 | A | 8/1972 | Matsuda |
| 4,044,769 | A | 8/1977 | Papajohn |
| 4,205,679 | A | 6/1980 | Repke et al. |
| 4,352,356 | A | 10/1982 | Tong |
| 4,355,425 | A | 10/1982 | Jones et al. |
| 4,560,381 | A | 12/1985 | Southwell |
| 4,781,962 | A | 11/1988 | Zamarripa et al. |

(Continued)

FOREIGN PATENT DOCUMENTS

| | | |
|---|---|---|
| AU | 2006209375 A1 | 10/2006 |
| AU | 2014218471 B2 | 10/2016 |

(Continued)

OTHER PUBLICATIONS

English-language machine translation of Japan Patent Application Publication No. JP2005154922, Jun. 16, 2005.

(Continued)

*Primary Examiner* — Michele Kidwell
(74) *Attorney, Agent, or Firm* — Kolitch Romano Dascenzo Gates LLC

(57) ABSTRACT

Garments include a fluid retention assembly coupled to an interior side of a garment base, with said coupling not being present on an exterior side of the garment base. The fluid retention assembly includes two fluid-retention zones of different absorbencies. One or more fluid retention assemblies may be located anywhere on the garment, without being limited to positioning near edges or apertures. A moisture-impermeable layer of the fluid retention assembly separates the interior side of the garment base from the fluid retention zones, such that the moisture-impermeable layer is configured to restrict and/or at least substantially prevent fluid from exiting the fluid retention assembly to the exterior side of the garment base.

23 Claims, 13 Drawing Sheets

(56) References Cited

U.S. PATENT DOCUMENTS

| | | |
|---|---|---|
| 4,813,950 A | 3/1989 | Branch |
| 4,847,134 A | 7/1989 | Fahrenkrug et al. |
| 4,898,594 A | 2/1990 | Cottenden |
| 5,151,092 A | 9/1992 | Buell et al. |
| 5,167,897 A | 12/1992 | Weber et al. |
| 5,217,782 A | 6/1993 | Moretz et al. |
| 5,224,941 A | 7/1993 | Simmons |
| 5,308,346 A | 5/1994 | Sneller et al. |
| 5,342,338 A | 8/1994 | Roe |
| 5,360,420 A | 11/1994 | Cook et al. |
| 5,368,910 A | 11/1994 | Langdon |
| 5,411,498 A | 5/1995 | Fahrenkrug et al. |
| 5,449,352 A | 9/1995 | Nishino et al. |
| 5,500,270 A | 3/1996 | Langdon et al. |
| 5,507,895 A | 4/1996 | Suekane |
| 5,518,801 A | 5/1996 | Chappell et al. |
| 5,664,452 A | 9/1997 | Langdon et al. |
| 5,677,028 A | 10/1997 | Ravella |
| 5,693,169 A | 12/1997 | Langdon et al. |
| H1732 H | 6/1998 | Johnson |
| H1746 H | 8/1998 | Carrier et al. |
| 5,851,204 A | 12/1998 | Mizutani |
| 5,855,573 A | 1/1999 | Johansson |
| 5,879,487 A | 3/1999 | Ravella |
| 5,899,895 A | 5/1999 | Robles et al. |
| 5,921,974 A | 7/1999 | Kikuchi |
| 6,117,523 A | 9/2000 | Sugahara |
| 6,120,487 A | 9/2000 | Ashton |
| 6,149,497 A | 11/2000 | Smith |
| 6,174,303 B1 | 1/2001 | Suprise et al. |
| 6,192,521 B1 | 2/2001 | Alberts et al. |
| 6,231,554 B1 | 5/2001 | Menard |
| 6,240,569 B1 | 6/2001 | Von Gompel et al. |
| 6,355,330 B1 | 3/2002 | Koslow et al. |
| 6,381,994 B1 | 5/2002 | Lee |
| 6,383,960 B1* | 5/2002 | Everett ............... A61F 13/535 442/317 |
| 6,569,139 B1* | 5/2003 | Datta ............... A61F 13/49017 604/385.27 |
| 6,610,901 B2* | 8/2003 | McMahon-Ayerst ........ A61F 13/66 604/378 |
| 6,622,312 B2 | 9/2003 | Rabinowicz |
| 6,626,883 B2 | 9/2003 | Wada et al. |
| 6,807,685 B1 | 10/2004 | Hasegawa et al. |
| 6,848,121 B1 | 2/2005 | Halid |
| 6,861,520 B1 | 3/2005 | Todd et al. |
| 7,008,887 B2 | 3/2006 | Rearick et al. |
| 7,083,604 B2 | 8/2006 | Sakaguchi |
| 7,156,828 B2 | 1/2007 | Ostrow |
| RE39,919 E | 11/2007 | Dodge et al. |
| 7,322,966 B1 | 1/2008 | Deerin |
| 7,393,346 B2* | 7/2008 | Morman ............ A61F 13/51464 604/385.01 |
| 7,686,794 B2 | 3/2010 | Mitchell |
| 7,951,128 B1 | 5/2011 | Lewis |
| 8,052,665 B2 | 11/2011 | Wastlund-Karlsson et al. |
| 8,058,343 B2 | 11/2011 | Liu et al. |
| 8,117,675 B2 | 2/2012 | Strange et al. |
| 8,282,618 B2 | 10/2012 | Nordness et al. |
| 8,460,265 B1 | 6/2013 | Calender |
| D701,018 S | 3/2014 | Wexler |
| D716,020 S | 10/2014 | Dunbar et al. |
| 8,935,813 B2 | 1/2015 | O'Leary |
| 9,011,398 B2* | 4/2015 | Johnston ............ A61F 13/55105 604/385.19 |
| 9,301,551 B2 | 4/2016 | Back et al. |
| 10,226,388 B2 | 3/2019 | Nelson |
| 10,335,325 B2 | 7/2019 | Sheldon et al. |
| 10,441,479 B2 | 10/2019 | Griffiths |
| 10,441,480 B2 | 10/2019 | Griffiths |
| 10,575,573 B2 | 3/2020 | Griffiths |
| 10,765,564 B2 | 9/2020 | Lee et al. |
| 10,897,941 B1 | 1/2021 | Smoter |
| 10,905,596 B2 | 2/2021 | Sina et al. |
| 11,154,431 B1 | 10/2021 | Yip et al. |
| 11,207,225 B2 | 12/2021 | Kajanthan et al. |
| 11,253,017 B2 | 2/2022 | Friedrich |
| D948,167 S | 4/2022 | Carpenter et al. |
| 11,331,229 B2 | 5/2022 | Lee et al. |
| 11,395,774 B2 | 7/2022 | Skinner et al. |
| 11,497,263 B1 | 11/2022 | Deshaies et al. |
| 11,553,739 B2 | 1/2023 | Henry |
| 11,590,034 B2 | 2/2023 | Deshaies et al. |
| 11,701,267 B2 | 7/2023 | Greco et al. |
| 2001/0031957 A1 | 10/2001 | Prestley et al. |
| 2002/0016580 A1 | 2/2002 | Wada et al. |
| 2002/0129434 A1 | 9/2002 | Rabinowicz |
| 2002/0177829 A1 | 11/2002 | Fell et al. |
| 2003/0004488 A1 | 1/2003 | Ashton et al. |
| 2003/0124927 A1 | 7/2003 | Waldroup et al. |
| 2003/0143376 A1 | 7/2003 | Toyoshima et al. |
| 2004/0229008 A1 | 11/2004 | Hoying |
| 2004/0265533 A1 | 12/2004 | Hoying et al. |
| 2005/0055002 A1 | 3/2005 | Whitelaw et al. |
| 2005/0090790 A1 | 4/2005 | Veith |
| 2005/0131365 A1 | 6/2005 | Sakaguchi |
| 2005/0197643 A1 | 9/2005 | Suga et al. |
| 2006/0070163 A1 | 4/2006 | Beck et al. |
| 2008/0108962 A1 | 5/2008 | Furuta et al. |
| 2008/0110775 A1 | 5/2008 | Beck et al. |
| 2008/0222781 A1 | 9/2008 | Rhew |
| 2008/0275415 A1 | 11/2008 | Wheeler et al. |
| 2008/0276352 A1 | 11/2008 | Strange et al. |
| 2009/0240224 A1 | 9/2009 | Underhill et al. |
| 2009/0247977 A1 | 10/2009 | Takeuchi et al. |
| 2010/0222759 A1 | 9/2010 | Hammons et al. |
| 2010/0249736 A1 | 9/2010 | Png et al. |
| 2011/0048077 A1 | 3/2011 | Warren et al. |
| 2011/0172621 A1 | 7/2011 | Lee et al. |
| 2011/0224639 A1 | 9/2011 | Venable |
| 2012/0123377 A1 | 5/2012 | Back |
| 2013/0006209 A1 | 1/2013 | Ruiz |
| 2013/0072888 A1 | 3/2013 | Zorin |
| 2013/0125293 A1 | 5/2013 | Stearns |
| 2014/0039432 A1 | 2/2014 | Dunbar et al. |
| 2014/0378935 A1 | 12/2014 | Arayama et al. |
| 2016/0089276 A1 | 3/2016 | Griffiths |
| 2016/0184146 A1 | 6/2016 | Tulk et al. |
| 2018/0014983 A1 | 1/2018 | Jayasuriya et al. |
| 2019/0380886 A1 | 12/2019 | Hammond |
| 2020/0000155 A1 | 1/2020 | Etienne |
| 2020/0000649 A1 | 1/2020 | Griffiths |
| 2020/0222256 A1 | 7/2020 | Chong |
| 2021/0015684 A1 | 1/2021 | Nakabugo |
| 2021/0030605 A1 | 2/2021 | Kajanthan et al. |
| 2021/0100698 A1* | 4/2021 | Langdon ............ A61F 13/51456 |
| 2021/0177676 A1* | 6/2021 | Kajanthan ............ A41D 31/10 |
| 2021/0282469 A1 | 9/2021 | Siriwardena |
| 2021/0290447 A1 | 9/2021 | Sepello et al. |
| 2021/0298369 A1 | 9/2021 | Polstein et al. |
| 2022/0117790 A1 | 4/2022 | Locke et al. |
| 2022/0117792 A1 | 4/2022 | Bradford |
| 2022/0133544 A1 | 5/2022 | Turton et al. |
| 2022/0160552 A1 | 5/2022 | Carpenter |
| 2022/0211558 A1 | 7/2022 | Kajanthan et al. |
| 2022/0249303 A1* | 8/2022 | Yang ............... A61F 13/51121 |
| 2022/0256938 A1* | 8/2022 | King ............... A41B 9/12 |
| 2022/0354710 A1 | 11/2022 | Sepello et al. |
| 2022/0408848 A1 | 12/2022 | Krupa |
| 2023/0010999 A1 | 1/2023 | Sieck et al. |
| 2023/0128088 A1 | 4/2023 | Deshaies et al. |
| 2023/0129586 A1 | 4/2023 | Greco et al. |
| 2023/0225437 A1 | 7/2023 | Carlino et al. |
| 2024/0032609 A1 | 2/2024 | Power et al. |

FOREIGN PATENT DOCUMENTS

| | | |
|---|---|---|
| CA | 2126280 A1 | 12/1994 |
| CA | 2126281 A1 | 12/1994 |
| CA | 2152135 A1 | 12/1995 |
| EP | 1370161 A1 | 12/2003 |
| JP | 2005154922 A | 6/2005 |

(56) References Cited

FOREIGN PATENT DOCUMENTS

| | | |
|---|---|---|
| JP | 2005154924 A | 6/2005 |
| KR | 20070018490 A | 2/2007 |
| KR | 100694187 B1 | 3/2007 |
| WO | 1997046198 A1 | 12/1997 |
| WO | 2006036841 A1 | 4/2006 |
| WO | 2021160627 A1 | 8/2021 |
| WO | 2024012672 A1 | 1/2024 |

OTHER PUBLICATIONS

English-language machine translation of Japan Patent Application Publication No. JP2005154924, Jun. 16, 2005.

English-language machine translation of Korea Patent No. KR100694187, Mar. 6, 2007.

English-language machine translation of Korea Patent Application Publication No. KR20070018490, Feb. 14, 2007.

"Bemis SewFree" webpage (www.bemisheatseal.com/Sewfree.htm), 2 pages, available at least as early as Aug. 4, 2001, retrieved from Internet Archive Wayback Machine (https://web.archive.org/web/20010804041402/http://www.bemisheatseal.com:%2080/Sewfree.htm) on Jan. 29, 2021.

Lo, T.Y., "Techtextil/Avantex 2005 (2)" Textile Asia, 2005, pp. 26-27.

Isaacs, Mac, "Seamless: Eliminating Stitches—More Than a Buzzword," AATCC Review, Nov. 2005, pp. 16-19.

Bemis Associates, Sewfree Adhesive Films for Intimate Apparel, 2013, 8 pages.

Photographs of Adidas Techfit Period-Proof Biker Short Tights, ordered Jun. 24, 2021.

Photographs Lilova Seamless High Waist, ordered Oct. 12, 2021.

Photographs Lilova Swimwear One-Piece Classic, ordered Oct. 12, 2021.

Photographs of Modibodi Seamfree Bikini Moderate-Heavy, ordered Feb. 9, 2022.

Photographs of Proof Leakproof Hipster Underwear, ordered Aug. 7, 2020.

Photographs of Pure Rosy Banded Brief—Jam, ordered Oct. 12, 2021.

Photographs of Ruby /Love Period Underwear Bikini—Pretty in Pink, ordered May 6, 2021.

Photographs of SPEAX by Thinx Hiphugger Women's Underwear—Leakproof, Breathable—M—Beige, ordered Feb. 7, 2020.

Photographs of TomboyX Leakproof Bikini—Plum, ordered Nov. 10, 2020.

Swantko, Kathlyn, "Forming A New Bond," FabricTrends: A GearTrends Supplement, 2004, pp. 12-14.

Photographs of Neiwai Pantie Pro Low Waist Period Brief, purchased Dec. 11, 2023.

\* cited by examiner

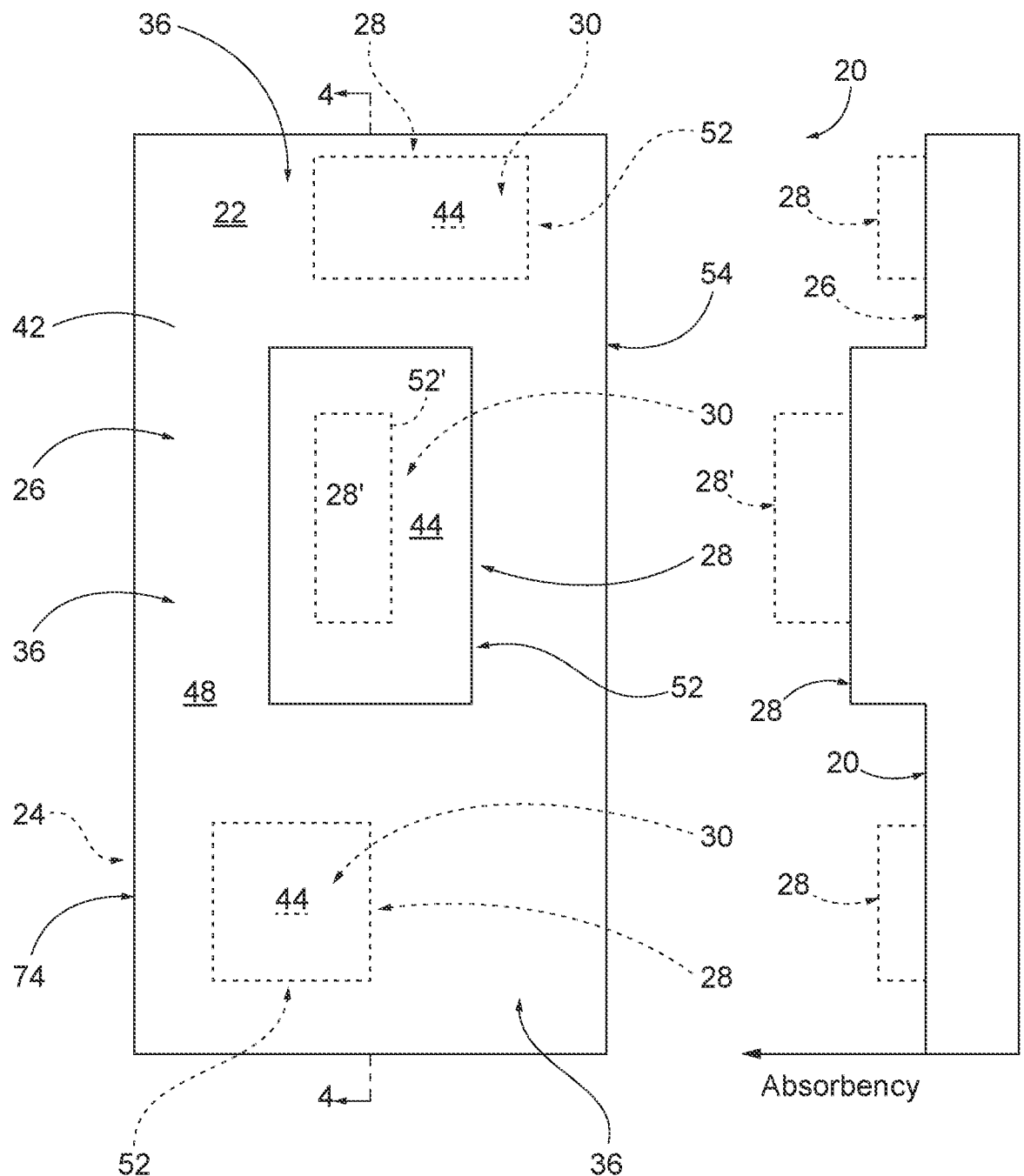

GARMENTS WITH FLUID RETENTION ASSEMBLIES AND RELATED METHODS

FIELD

The present disclosure relates to garments with fluid retention assemblies and related methods.

BACKGROUND

Garments and other wearable accessories that are configured to be worn adjacent to a wearer's skin sometimes exhibit moisture-absorbing properties, such as to absorb and/or retain menstrual fluids and/or urine produced by the user. Such garments may absorb and retain such fluids in a discreet and leak-proof manner, such as to hide such fluids from view and/or to enhance the wearer's comfort. However, many such garments include absorbent regions that are bulky and thus uncomfortable and/or difficult to conceal. Additionally, conventional attachment of the absorbent regions to the main body of the garment may result in leakage and/or bulkiness, at the expense of the wearer's comfort and the discreetness of the garment.

To address these considerations, several prior art undergarments include absorbent regions that are bonded and/or laminated to a main body portion of the undergarment, though this bonding typically extends all the way through the main body portion of the garment. As a result, the arrangement of such bonds may be insufficient to fully protect against moisture exiting and/or entering the undergarment. Additionally, such constructions may be incompatible with garment applications other than traditional undergarments, in view of the absorbent regions and/or their outlines being visible on the exterior of the garment due to the way the absorbent regions are attached to the main body in such conventional garments.

SUMMARY

Presently disclosed garments and methods of manufacture may be formed to avoid the disadvantages of prior art garments with absorbent regions, and may include two or more fluid-retention zones having different absorbencies to provide an increased overall absorbency level of the garment while minimizing bulkiness. Additionally or alternatively, presently disclosed garments may include a fluid retention assembly that is bonded only to an interior side of a garment base, such that there is no bonding or stitching on an exterior side of the garment base that corresponds to the fluid retention assembly, thereby preserving discreetness and overall aesthetic appeal in the garment.

In one example according to the present disclosure, a garment comprises a garment base and a fluid retention assembly coupled to an interior side of the garment base. The fluid retention assembly comprises a first fluid-retention zone, a second fluid-retention zone having a greater absorbency per unit area than the first fluid-retention zone, and a moisture-impermeable layer configured to restrict fluid from exiting the fluid retention assembly to an exterior side of the garment base.

BRIEF DESCRIPTION OF THE DRAWINGS

FIG. 3 is a schematic top plan view of examples of fluid retention assemblies according to the present disclosure.

FIG. 4 is a schematic representation of different relative amounts of absorbency that may be provided in different zones of absorbency of the example fluid retention assemblies of FIG. 3.

DESCRIPTION

Figure 1:
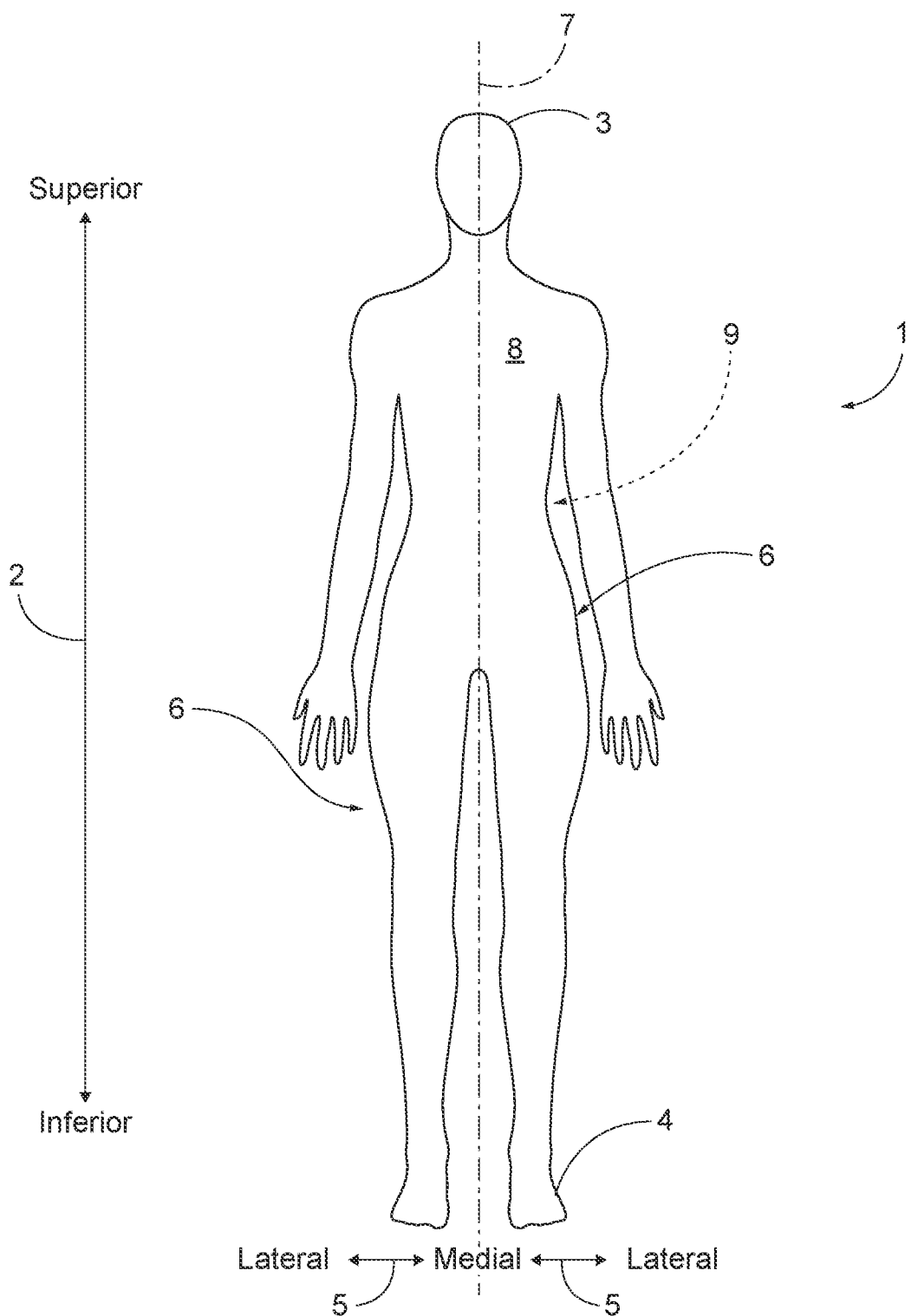
FIG. 1 is a representation of a generic human figure, providing reference direction indications for use in the specification.

FIG. 1 provides a general reference framework for discussion of presently disclosed garments, with reference to a wearer 1. As indicated by arrow 2, a first component or feature of the disclosed garments may be described as being superior relative to another component or feature, or relative to an aspect of wearer 1, if the first component or feature is closer to the head 3 of wearer 1. Similarly, a first component or feature of the disclosed garments may be described as being inferior relative to another component or feature, or relative to an aspect of wearer 1, if the first component or feature is closer to the feet 4 of wearer 1.

As indicated by arrows 5, a first component or feature of the disclosed garments may be described as being lateral to another component or feature, or to an aspect of wearer 1, if the first component or feature is closer to a side 6 of wearer 1 than is the other component or feature. Likewise, a first component or feature of the disclosed garments may be described as being medial to another component or feature, or to an aspect of wearer 1, if the first component or feature is closer to an imaginary centerline 7 of wearer 1 than the other component or feature. Put another way, a first component or feature is medial to a second component or feature if the first component or feature is closer to imaginary centerline 7 than the second component or feature is, whereas a first component or feature is lateral to a second component or feature if the first component or feature is closer to a given side 6 than is the second component or feature. Thus, generally, if a first component or feature is lateral to a second component or feature, then the second component or feature will likewise be medial to the first component or feature.

Components or features of disclosed garments also may be described relative to an anterior side and a posterior side of the garments. As used herein, the anterior side of garments refers to the side of the garment that is configured to be positioned on the wearer's anterior side 8 (e.g., the front half of the wearer's body) when the garment is worn. Similarly, the posterior side of garments refers to the side of the garment that is configured to be positioned on the wearer's posterior side 9 (e.g., the back half of the wearer's body).

As represented in FIG. 1 and as described herein, the various elements of garments disclosed herein may be described in terms of relative positions to each other when such garments are worn, or donned, by a wearer, when the wearer is standing vertically, and from the perspective of the wearer. Such terms may include terms such as "above," "below," "upper," "lower," "front," "back," "behind," and similar. Accordingly, when describing a first element as being above or below a second element, the first element falls in a horizontal plane that is above or below a horizontal plane in which the second element falls, but the first element is not necessarily directly above or below the second element along a vertical vector.

Furthermore, an "edge" of an element of disclosed garments, as used herein, additionally or alternatively may be referred to as, or described as, an edge region, a margin, or a boundary of the element, and an "edge" is not necessarily the absolute two-dimensional terminus of the element. For example, as typical in garment construction, seams may have a width to them, and the region associated with a seam may be considered the "edge" of the element. Moreover, two panels or sections of material being secured together at a seam often are not perfectly aligned along their terminuses. Moreover, a seam within an expanse of material may define an "edge" of a sub-portion of that expanse of material, with the sub-portion optionally being described as a "panel" or "region" of the material. In other words, two adjacent panels or regions may, in some cases, be constructed of the same piece of material with a seam or other structure defining an edge, or boundary, between the two adjacent panels.

FIGS. 2-4, and 9-10 provide schematic representations of non-exclusive examples of garments 10, or potential components or aspects thereof, according to the present disclosure. Elements that serve a similar, or at least substantially similar, purpose are labeled with like numbers in each of FIGS. 2-4 and, 9-10, and these elements may not be discussed in detail herein with reference to each of FIGS. 2-4 and, 9-10. Similarly, all elements may not be labeled in each of FIGS. 2-4 and 9-10, but reference numerals associated therewith may be utilized herein for consistency. Elements, components, and/or features that are discussed herein with reference to one or more of FIGS. 2-4 and 9-10 may be included in and/or utilized with any of FIGS. 2-4 and 9-10 without departing from the scope of the present disclosure. In general, elements that are likely to be included in a given (i.e., a particular) example are illustrated in solid lines, while elements that are optional to a given example are illustrated in dashed lines. However, elements that are shown in solid lines are not essential to all examples, and an element shown in solid lines may be omitted from a particular example without departing from the scope of the present disclosure.

Figure 2:
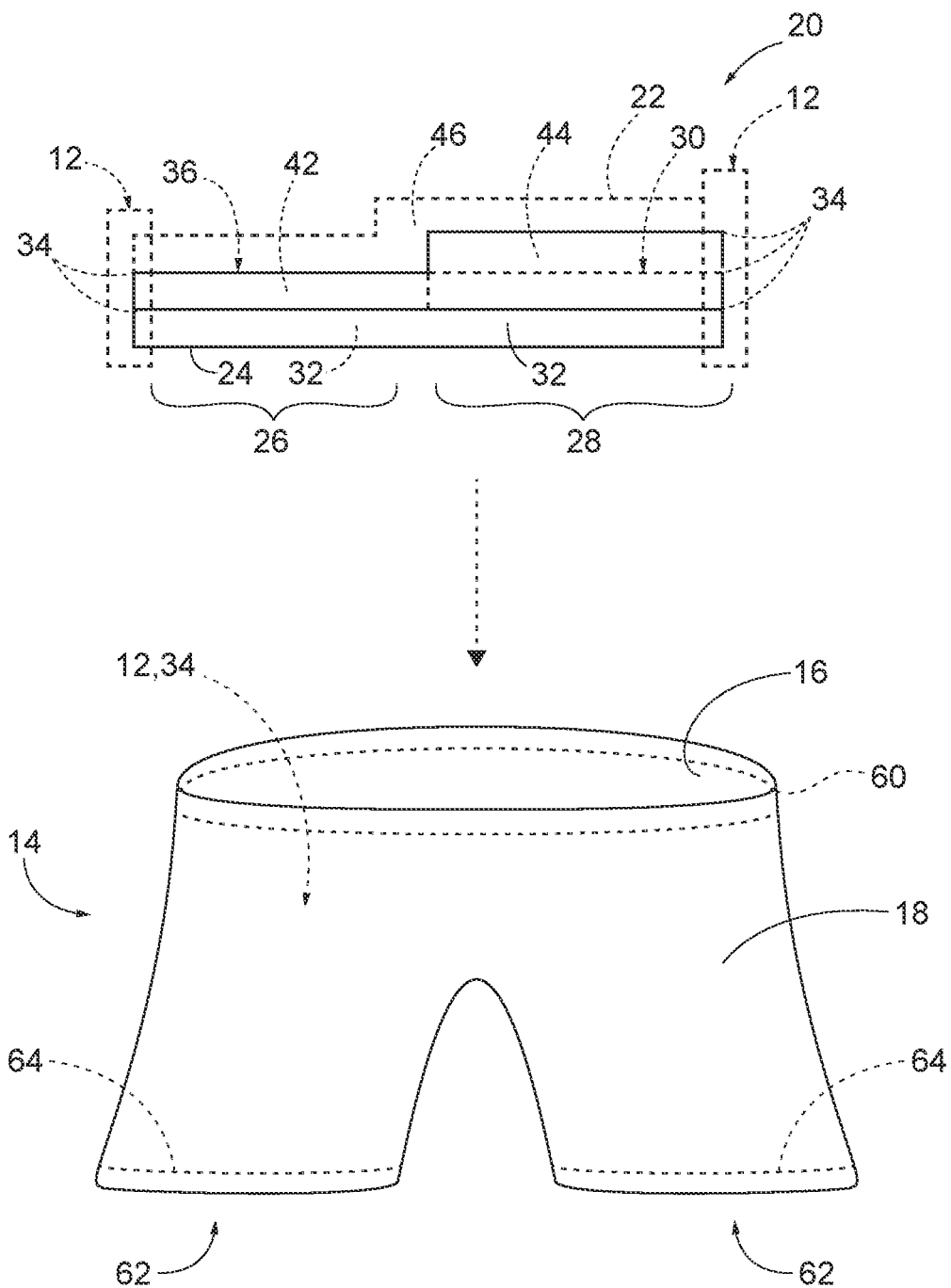
FIG. 2 is an exploded schematic representation of examples of garments according to the present disclosure, shown from the front of the garment.

FIG. 2 is a schematic exploded representation of illustrative examples of garments 10 according to the present disclosure. While garment 10 is represented in FIG. 2 as a lower body garment, garments 10 according to the present disclosure may include upper body garments (e.g., tops, shirts, sweaters, sweatshirts, bras, sports bras etc.); lower body garments (e.g., bottoms, shorts, tights, leggings, hosiery, pants, skorts, skirts, underwear, briefs, swim bottoms, etc.); full body garments (e.g., rompers, dresses, jumpsuits, onesies, swimsuits, etc.); or other types of garments or wearable accessories (e.g., hats, scarves, neck gaiters, sweat bands, etc.). Garments 10 may be configured to be worn as outer wear, or as undergarments. Garments 10 may be configured as activewear garments, intended be worn while exercising or participating in physical activity. Garments 10 generally are configured to be washed and re-worn numerous times.

Garments 10 generally include a garment base 14 and a fluid retention assembly 20, which is schematically represented in cross-section in FIG. 2 for illustrative purposes. Garment base 14 has an interior side 16 and an exterior side 18, with interior side 16 being configured to face the wearer when garment 10 is worn by the wearer, and exterior side 18 being configured to face outwardly away from the wearer when garment 10 is worn. In particular, in some examples, at least a portion of the garment's interior side 16 is configured to directly contact the wearer's skin when garment 10 is worn by the wearer. Stated differently, in some examples, garment 10 is configured such that, when the garment is worn by the wearer, no portion of the garment is positioned directly between the garment's interior side 16 and the wearer's body. Similarly, in some examples, garment 10 is configured such that, when the garment is worn by the wearer, no portion of the garment is positioned distal the wearer relative to the garment's exterior side 18.

Fluid retention assembly 20 is coupled to interior side 16 of garment base 14. Fluid retention assembly 20 includes an assembly interior side 22 that is configured to face the wearer when garment 10 is worn. For example, assembly interior side 22 may be configured to contact the wearer's skin, may be placed adjacent to the wearer's body when garment 10 is worn, and/or may be nearer to the wearer's body when garment 10 is worn than is an assembly exterior side 24 of fluid retention assembly 20. Thus, assembly exterior side 24 may be configured to face outwardly away from the wearer when garment 10 is worn. Assembly exterior side 24 generally faces interior side 16 of garment base 14 when fluid retention assembly 20 is coupled to garment base 14.

Fluid retention assembly 20 may have any of a variety of constructions for absorbing and capturing fluids, liquids, or moisture from the wearer. Fluid retention assembly 20 includes at least a first fluid-retention zone 26 having a first-zone absorbency, and a second fluid-retention zone 28 having a second-zone absorbency that differs from (e.g., greater than or less than) the first-zone absorbency, where absorbency is measured as a volume of liquid at saturation per area across an expanse of the respective zone (e.g., when viewed from a top, plan view). Fluid retention assembly 20 also includes one or more moisture-impermeable layers 32 that are configured to restrict passage of liquid therethrough. Moisture-impermeable layer 32 may be an independent layer from the fluid retention zones. Additionally or alternatively, first fluid-retention zone 26 and/or second fluid-retention zone 28 may include a respective moisture-impermeable layer 32, and/or a moisture-impermeable material, coating, and/or treatment. Garments 10 may additionally include additional fluid retention zones as well.

The fluid retention zones of a garment 10 may be constructed in various manners to result in different levels of fluid absorption amongst the fluid retention zones. For example, the second fluid retention zone 28 may correspond to a region of overlap between two layers or material. Additionally, or alternatively, the second fluid retention zone 28 may be thicker than the first fluid retention zone 26. In other examples, the second fluid retention zone 28 may be constructed of a more absorbent material than the first fluid retention zone 26.

The use of different fluid retention zones 26, 28 in presently disclosed garments 10 may enable an increase in overall absorbency of fluid retention assembly 20, as compared to prior art absorbent garments, without creating bulkiness or increasing the overall thickness of the garment. In addition, because fluid can disperse in many directions depending on the position of the wearer (e.g., lying down on their back, or lying down on their stomach), the use of different fluid retention zones 26, 28 can help provide greater leak protection by being present in different areas of garment 10. For example, one or more second fluid retention zones 28 may be configured (i.e., positioned) to provide a targeted, centralized, or localized leak protection in one or more desired areas, such as in one more areas where the most fluid is expected to leave the body of the wearer.

Moisture-impermeable layer(s) 32 are positioned with respect to garment base 14 such that moisture-impermeable layer(s) 32 separate interior side 16 of garment base 14 from first fluid-retention zone 26 and one or more second fluid-retention zones 28. In this manner, moisture-impermeable layer(s) 32 are configured to restrict and/or at least substantially prevent fluid from passing through and exiting fluid retention assembly 20 to exterior side 18 of garment base 14. In other words, fluid retention assembly 20 may be configured to retain fluids excreted by the wearer (e.g., within fluid retention zones 26, 28), and restrict or prevent them from soaking through to exterior side 18 of garment base 14, thereby allowing garment 10 to be configured as a leak-proof or leak-resistant garment in areas corresponding to fluid retention assembly 20. In some examples, moisture-impermeable layer(s) 32 define assembly exterior side 24 of fluid retention assembly 20. In other examples, assembly exterior side 24 of fluid retention assembly 20 may be defined by an external layer configured to sandwich the one or more moisture-impermeable layers 32 between the external layer and first fluid-retention zone 26 and one or more second fluid retention zones 28.

Garment 10 may include one or more bonded regions 12 each having a plurality of adhesive bonds 34. As discussed in further detail herein, fluid retention assembly 20 may be bonded to garment 10, such as to interior side 16 of garment base 14 within a bonded region 12 via a plurality of adhesive bonds 34. In some examples, fluid retention assembly 20 is bonded to interior side 16 of garment base 14 in such a way that exterior side 18 of garment base 14 is free from seams or bonds along an assembly perimeter 74 of fluid retention assembly 20, which may contribute to the aesthetic appeal of disclosed garments 10. In some examples, a pre-formed fluid retention assembly 20 may be bonded to garment base 14, with fluid retention assembly 20 being pre-formed by bonding together the layers forming fluid retention assembly 20. The bonded construction of garment 10 as disclosed herein may allow for garment 10 to be low-profile and discreet without compromising the leak-proof properties of the garment. Each of the plurality of adhesive bonds 34 may operate to bond any of a variety of portions and/or components of garment 10 to one another.

In some examples, fluid retention assembly 20 is coupled to garment base 14 in a way that is substantially invisible to a non-wearer's eye when the non-wearer observes the garment when worn by the wearer. In other words, fluid retention assembly 20 may be coupled to interior side 16 of garment base 14 with said coupling not being present on exterior side 18 of garment base 14. For example, stitching used to couple fluid retention assembly 20 to garment base 14 may be configured to not extend all the way through garment base 14, such that it is not present on exterior side 18 of garment base 14. Additionally or alternatively, adhesive bonds 34 used to couple fluid retention assembly 20 to garment base 14 may be positioned only on interior side 16 of garment base 14, such that the adhesive bonds are not present on exterior side 18 of garment base 14. Put yet another way, exterior side 18 of garment base 14 may be continuous, without interruption by bonds or seams on exterior side 18 of garment 10, at least in areas corresponding to the location(s) of one or more fluid retention assemblies 20.

As schematically represented in FIG. 2, fluid retention assembly 20 may include a first absorbent layer 42 and a second absorbent layer 44, such that a region of overlap between the first absorbent layer 42 and the second absorbent layer 44 defines the second fluid-retention zone 28 and such that the portion of the first absorbent layer 42 not overlapped with the second absorbent layer 44 defines the first fluid-retention zone 26. The second absorbent layer 44 may be positioned to overlay (i.e., toward the wearer relative to) or underlie (i.e., away from the wearer relative to) first absorbent layer 42. First absorbent layer 42 and/or second absorbent layer 44 may additionally include, or be fused with or bonded to, a respective moisture-impermeable layer 32, or other moisture-impermeable material, coating, or treatment. In other examples, first fluid-retention zone 26 may be a thinner section of an absorbent layer, and second fluid-retention zone may be a thicker section of the absorbent layer. In some examples, the absorbent layer may taper in thickness between first fluid-retention zone 26 and second fluid-retention zone 28.

As schematically represented in FIG. 3 (which shows a top plan representation of examples of fluid retention assembly 20), in some examples, second absorbent layer 44 is overlaid on a first portion 30 of first absorbent layer 42 to form second fluid-retention zone 28, such that first portion 30 of first absorbent layer 42 is sandwiched between second absorbent layer 44 and assembly exterior side 24 of fluid retention assembly 20. However, as discussed, second absorbent layer 44 alternatively may underlie first absorbent layer 42, such that second absorbent layer 44 is sandwiched between first absorbent layer 42 and assembly exterior side 24. As shown in FIG. 3, a second portion 36 of first absorbent layer 42 may be free from overlap by second absorbent layer 44. Fluid retention assembly 20 may include a plurality of second fluid-retention zones 28. In examples including two or more second fluid-retention zones 28, the second fluid-retention zones 28 may be spaced apart from one another in various areas of first fluid-retention zone 26, corresponding to various portions 30 of first absorbent layer 42, as schematically and optionally represented in FIG. 3. That is, additional second fluid-retention zones 28 may be formed by overlaying (or underlaying) second absorbent layer 44 onto (or underneath) first absorbent layer 42 in the desired areas of fluid retention assembly 20. One or more additional fluid-retention zones also may be formed by overlaying or underlaying a portion of one or more additional absorbent layers with another absorbent layer (e.g., to form a three-layer absorbent zone), such as schematically and optionally illustrated at 28' in FIG. 3. Such additional absorbent layers may be stacked, or built up on one another, to create localized areas of increased absorption. Additionally or alternatively, garment 10 may include a plurality of fluid retention assemblies 20 spaced apart from one another, and/or a plurality of first fluid-retention zones 26.

FIG. 4 schematically represents the absorbency along line 4-4 in FIG. 3 of example fluid retention assemblies 20. As discussed, in some examples, absorbent layers may be stacked, or layered, to create localized areas of increased absorbency. For example, FIG. 3 illustrates in solid lines a single first fluid-retention zone 26 and a single second fluid-retention zone 28. In dashed lines, FIG. 3 illustrates two additional second fluid-retention zones 28 and a third fluid-retention zone 28'. FIG. 4 illustrates the corresponding relative absorbency of these zones across an expanse of the fluid retention assembly 20 of FIG. 3.

With reference again to FIG. 3, first absorbent layer 42 may be described as having a first footprint defined by a first perimeter 54 (i.e., a flat plan view of outline of first absorbent layer 42), while each second absorbent layer 44 may be described as having a second footprint defined by a second perimeter 52. The respective second footprint of each respective second absorbent layer 44 may be smaller than the first footprint of first absorbent layer 42. In other words, in some examples of garment 10, each of one or more second absorbent layers 44 has a smaller area than first absorbent layer 42. In some examples, some or all of first perimeter 54 of first absorbent layer 42 substantially corresponds to assembly perimeter 74 of fluid retention assembly 20 (e.g., some or all of first perimeter 54 may define some or all of assembly perimeter 74); though in other examples, some or all of assembly perimeter 74 may be larger than some or all of first perimeter 54 of first absorbent layer 42. Additionally or alternatively, a portion of perimeter 52 of second absorbent layer 44 may correspond to or be aligned with (e.g., may be substantially collinear with) assembly perimeter 74. Put in context of garment 10 being placed on a wearer, in various examples, one absorbent layer may extend superiorly to another absorbent layer on the front and/or back side of garment 10, one absorbent layer may extend further laterally or medially than another absorbent layer on the front and/or back side of garment 10, and/or one absorbent layer may extend closer to one or more garment apertures 62 (e.g., the leg opening garment apertures 62 shown in FIG. 2) than another absorbent layer.

Herein, the term "aligned" or "collinear," as used to describe a relative position of a first edge relative to a second edge, generally refers to a configuration in which the first edge and the second edge are positioned at respective locations that are not substantially spatially separated from one another medially or laterally. However, it is to be understood that a description herein of two or more components as being "aligned" or "collinear" does not necessarily mean that the two or more components are exactly and/or precisely aligned or collinear with one another. For example, as known in the art, garment construction is not perfect, and the imprecision introduced by human- and/or machine-performed manufacturing can introduce slight misalignments between components that nominally are intended or designed to be aligned or collinear with one another. Accordingly, for the purposes of the present disclosure, the terms "aligned" and "collinear" are intended to encompass configurations in which the components are perfectly aligned or collinear, as well as configurations in which the components are slightly misaligned as a result of manufacturing tolerances.

Generally, garments 10 may include one or more such garment apertures 62, with garment apertures 62 being at least partially defined by garment base 14. While FIG. 2 illustrates an example in which each garment aperture 62 is configured to receive a leg of the wearer when garment 10 is worn, garments 10 additionally or alternatively may include one or more garment apertures 62 that define an arm opening that is configured to receive an arm of the wearer when garment 10 is worn by the wearer, a neck opening configured to receive the wearer's head therethrough when garment 10 is worn, a waist opening configured to receive the wearer's torso or waist region when garment 10 is worn, or various other apertures that may be included in various types of garments 10. Some examples of garment 10 include one or more edge reinforcing strips 64, which may be positioned adjacent to one or more garment apertures 62. Edge reinforcing strip(s) 64 may be bonded to garment base 14 with at least one adhesive bond of the plurality of adhesive bonds 34. In some examples, edge reinforcing strip(s) 64 may at least partially define and/or reinforce one or more garment apertures 62. Edge reinforcing strip 64 may be an elastic strip in some examples of garment 10. In particular, edge reinforcing strip 64 may be an elastic strip (e.g., a strip of elasticized fabric) configured to conform each leg opening or other garment aperture 62 to the wearer's leg. In particular, each edge reinforcing strip 64 may at least partially define the corresponding garment aperture 62 and/or the corresponding leg opening. Additionally or alternatively, in some examples, each edge reinforcing strip 64 may be described as lining the corresponding garment aperture 62 and/or the corresponding leg opening. In some examples, each edge reinforcing strip 64 is bonded to garment base 14 with a corresponding adhesive bond 34.

In some examples, second fluid-retention zone 28 is thicker than first fluid-retention zone 26. In some examples, first absorbent layer 42 is thicker or thinner than second absorbent layer 44. In some examples, first absorbent layer 42 is formed of a different material than second absorbent layer 44. In some examples, first absorbent layer 42 may be thicker than second absorbent layer 44, though the overall thickness of fluid retention assembly 20 may be greater in areas corresponding to second fluid retention zone 28 due to the combination, or stacking, of first absorbent layer 42 and second absorbent layer 44 in areas of second fluid retention zone 28. By including different fluid-retention zones 26, 28, distinct areas of garment 10 (e.g., distinct areas of fluid retention assembly 20) may be more absorbent than other areas. For example, garments 10 may be configured to have a higher absorbency or to absorb a larger volume of fluid in second fluid-retention zone 28 than in first fluid-retention zone 26. Thus, by customizing the size, position, orientation, thickness, and/or materials of first fluid-retention zone 26 and second fluid-retention zone 28, garments 10 may be tailored for different uses and/or use in various types of garments, with the absorbency of fluid retention assembly 20 being customizable and configured to be optimized for different applications without needlessly increasing bulkiness in the entire garment 10. In nonlimiting representative examples of garment 10, areas of fluid retention assembly 20 corresponding to first fluid-retention zone 26 may be configured to retain at least 1 teaspoon (5 milliliters [ml]), at least 2 teaspoons (10 ml), at least 3 teaspoons (15 ml), at least 4 teaspoons (20 ml), at least 5 teaspoons (25 ml), at least 10 teaspoons (50 ml), at least 15 teaspoons (75 ml), and/or at least 20 teaspoons (100 ml) of liquid or fluid excreted or produced by the wearer such that the liquid or fluid is at least substantially prevented from exiting fluid retention assembly 20 to exterior side 18 of garment base 14. Additionally or alternatively, areas of fluid retention assembly 20 corresponding to, or including, second fluid-retention zone 28 may be configured to retain at least 1 teaspoon (5 ml), at least 2 teaspoons (10 ml), at least 3 teaspoons (15 ml), at least 4 teaspoons (20 ml), at least 5 teaspoons (25 ml), at least 10 teaspoons (50 ml), at least 15 teaspoons (75 ml), and/or at least 20 teaspoons (100 ml) of liquid or fluid excreted from the wearer such that the liquid or fluid is at least substantially prevented from exiting fluid retention assembly 20 to exterior side 18 of garment base 14.

With reference again to FIG. 2, in some examples, fluid retention assembly 20 may include a moisture-wicking layer 46. In some examples, moisture-wicking layer 46 defines assembly interior side 22 of fluid retention assembly 20. For example, moisture-wicking layer 46 may be configured to be positioned against the wearer's skin when garment 10 is worn by the wearer. In particular, in such examples, moisture-wicking layer 46 may be configured to draw moisture away from the wearer, such as via capillary action, and to direct and/or convey the moisture or fluids to fluid retention zones 26, 28 of fluid retention assembly 20. In some examples, first fluid-retention zone 26 and/or second fluid-retention zone 28 is sandwiched between moisture-wicking layer 46 and moisture-impermeable layer 32. Specifically, in some examples, second portion 36 of first absorbent layer 42 is sandwiched between moisture-wicking layer 46 and moisture-impermeable layer 32, while first portion 30 of first absorbent layer 42 is sandwiched between second absorbent layer 44 and moisture-impermeable layer 32.

As noted above, garments 10 are not limited to lower body garments. In various types of garments 10 according to the present disclosure, one or more fluid retention assemblies 20 may be positioned in a region of garment 10 that is configured to be positioned on, adjacent to, and/or around the wearer's pelvic region (e.g., the wearer's crotch or groin region), armpit region, bra line region, torso region, back, shoulders, buttocks, legs, arms, chest, neck, nipples, and/or breast region when the garment is worn by the wearer. In specific examples, one or more fluid retention assemblies 20 are configured and positioned to absorb and retain various fluids excreted from the wearer or produced by the wearer while the wearer wears garment 10, such as urine, sweat, blood, menstrual fluids, excrement, breast milk, wound excretions, or other fluids. For example, first fluid retention zone 26 and second fluid retention zone 28 may be configured and positioned to address specific applications or uses of garment 10, such as by positioning second fluid retention zone 28 in areas where additional absorbency may be needed (e.g., where more fluid may be expected to leave the body of the user), while positioning first fluid retention zone 26 in areas where less absorbency may be needed. Fluid retention assemblies 20, or specifically first fluid retention zone 26 and second fluid retention zone 28, may be positioned as determined by the genitalia of the user, and/or by the predominant position the user is expected to be in while wearing garment 10. For example, fluid may exit the body in different positions, or may flow in different directions after exiting the body, when a user is predominantly supine or bedridden, or when a user is predominantly in a seated position, than when the user is standing or moving around or engaged in physical activity. For example, depending on the user's position, fluid may flow forwards or backwards when it leaves the body, but may be centralized in a middle area of garment 10. In another example, additional absorbency may be needed, for example, in areas of garment 10 configured to be positioned closest to the user's urethra or vagina, while areas of the garment 10 configured to be positioned further away from the urethra or vagina may require less absorbency. In some examples, it may be desirable to have more absorbency in the front of garment 10 than in the back, or vice versa, or about the same absorbency in both the front and back of garment 10. First fluid retention zone 26 and second fluid retention zone 28 may be positioned in various examples of garments 10 to address the specific needs and positioning created by different users and/or different body positions of the user while wearing garments 10.

Disclosed garments 10 may be configured to restrict such moisture or fluids from penetrating through garment 10 to reach exterior side 18 of garment base 14. Fluid retention assemblies 20 may be positioned in various types of garments to prevent seepage or leakage of bodily excretions from being visible on exterior side 18 of garment base 14. For example, fluid retention assemblies 20 may be placed on a given garment 10 in locations where the wearer might otherwise have visible sweat when undergoing physical activity, and/or fluid retention zones 26, 28 may be optimized for various types of incontinence or menstruation, and/or for absorbing breast milk leakage in nursing mothers. Other uses of disclosed fluid retention assemblies 20 also are within the scope of the present disclosure.

Various materials may be suitable for constructing disclosed garments 10. Materials described herein are not limiting, and included only for illustrative purposes. In some garments 10, first absorbent layer 42 and/or second absorbent layer 44 is formed of polyester nylon, though this is non-limiting, as many different materials may be suitable, with other non-exclusive examples including polyester, nylon, cotton, and/or other pulp-based fibers such as modal or bamboo. Moisture-wicking layer 46 of fluid retention assembly 20 may be formed of synthetic or natural fibers, with nonlimiting examples including, cotton, carbon cotton, carbon-cotton spandex, polyester, nylon, modal, and/or bamboo, among others. Suitable materials for moisture-wicking layer 46 may be configured to be quick-drying, odor-fighting, and/or anti-microbial, and/or may be treated or coated to achieve one or more of these properties. Moisture-wicking layer 46 may include a mesh material and/or a solid material. In some examples of garment 10, moisture-impermeable layer 32 may be a coating or treatment applied to outer surface 50 of first fluid-retention zone 26. Additionally or alternatively, moisture-impermeable layer 32 may be a leak-resistant or waterproof fabric or other moisture-barrier material; a moisture-barrier layer, a moisture-barrier film, a moisture-barrier membrane; a waterproof, water-resistant, or water-repellant treatment; and/or a waterproof, water-resistant, or water-repellant coating. Garment base 14 may be at least partially formed of one or more of a natural fiber, cotton, a synthetic fiber, polyester, nylon, Spandex™ fabric, and combinations thereof, and may include a plurality of base panels that are operatively coupled to one another.

Figure 5:
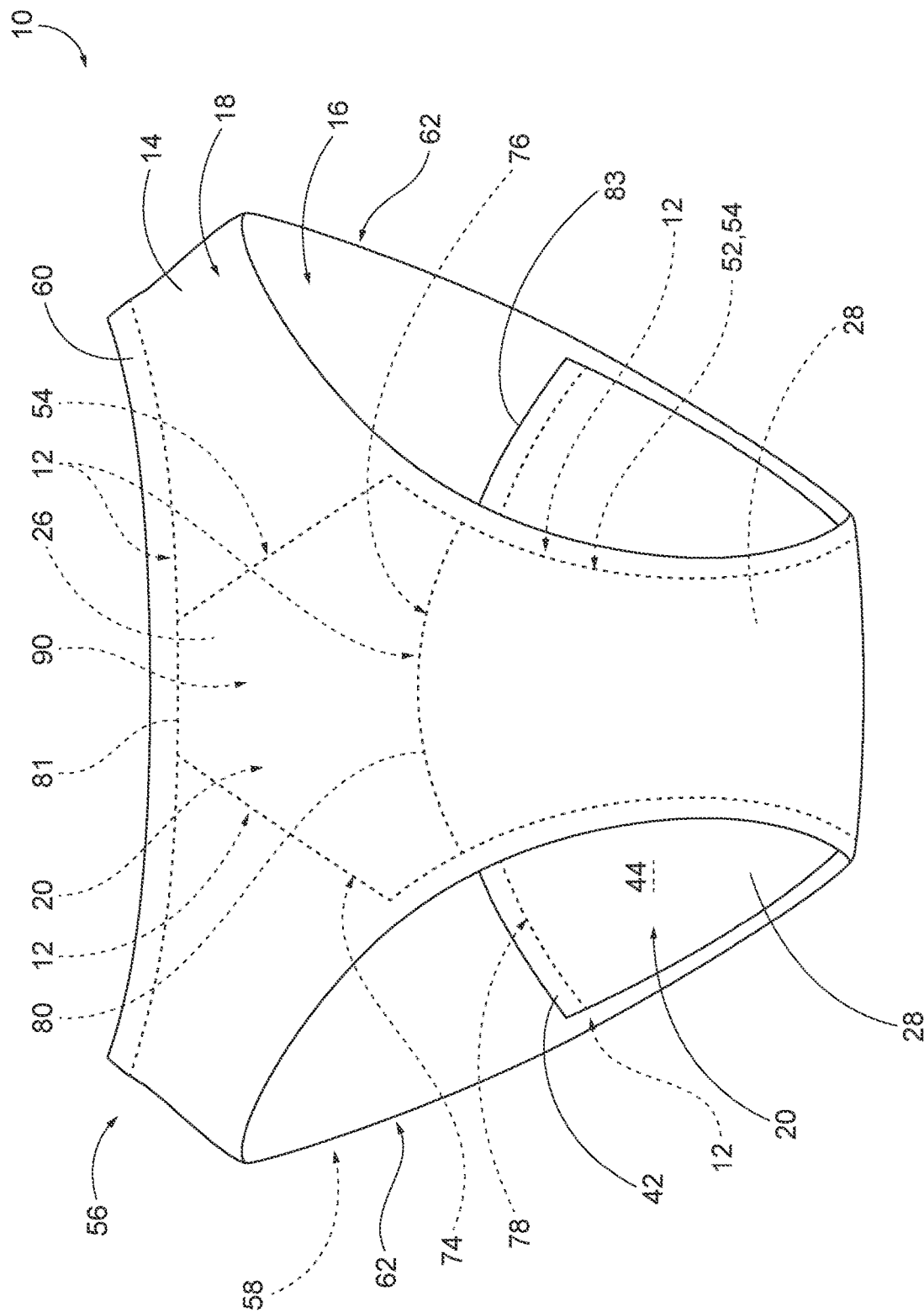
FIG. 5 is a front elevation view of an example of a garment including a fluid retention assembly, according to the present disclosure.
Figure 6:
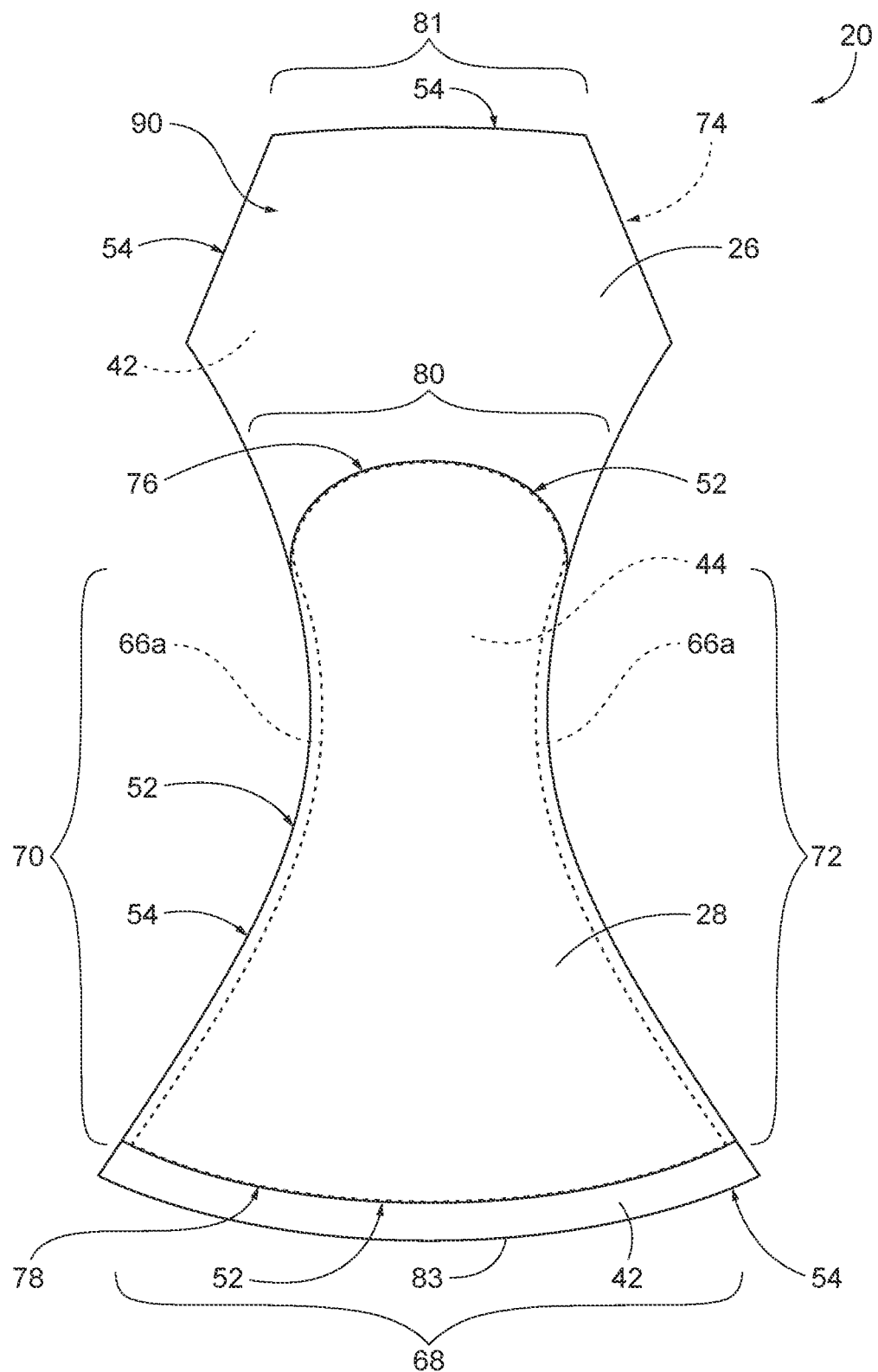
FIG. 6 is a top plan view of an example of fluid retention zones of a fluid retention assembly.

FIG. 5 is a front (e.g., anterior side) elevation view of an example of garment 10, and FIG. 6 is a top plan view of an example of fluid retention assembly 20 from garment 10 of FIG. 5, shown on its own and laid flat for clarity. FIG. 6 illustrates only an example of first fluid-retention zone 26 and second fluid-retention zone 28, without other potential layers of fluid retention assembly 20, to more clearly illustrate the example of fluid retention zones 26, 28. The example of garment 10 in FIG. 5 is shown as a pair of briefs, with garment apertures 62 in the form of two leg openings. Fluid retention assembly 20 is shown coupled to interior side 16 of garment base 14. Second absorbent layer 44 may extend superiorly to a lesser extent than does first absorbent layer 42 on an anterior side 56 of garment 10, as shown in FIG. 5. For example, as shown in FIG. 5, first absorbent layer 42 may extend superiorly to or near a waistband region 60 of garment 10, while a superior edge region 80 of footprint perimeter 52 of second absorbent layer 44 on anterior side 56 of garment 10 may be positioned inferiorly to waistband region 60, and/or inferiorly to a superior edge region 81 of footprint perimeter 54 of first absorbent layer 42. Fluid retention zones 26, 28 and absorbent layers 42, 44 are configured such that they may be positioned on garment 10 without needing to be adjacent to leg openings (or other openings, such as the waist opening of waistband region 60) of garment 10. This capability may enable disclosed fluid retention assemblies 20 to be incorporated in different types of garments for different types of wearers, meeting unique or specific needs of different wearers. Additionally or alternatively, second absorbent layer 44 may extend superiorly to a lesser extent than does first absorbent layer 42 on a posterior side 58 of garment 10, as shown in FIG. 5. In the example of FIG. 5, fluid retention assembly 20 does not extend superiorly to waistband region 60 on posterior side 58 of garment 10. While footprint perimeter 52 of second absorbent layer 44 is generally smaller than footprint perimeter 54 of first absorbent layer 42, in some examples, second fluid-retention zone 28 extends superiorly, inferiorly, medially, and/or laterally farther than first fluid-retention zone 26. Additionally or alternatively, first fluid-retention zone 26 may extend superiorly, inferiorly, laterally, and/or medially farther than second fluid-retention zone 28.

Garment base 14 may at least partially define waistband region 60, or waistband region 60 may be formed via an addition of material, such as a reinforcing strip. Garment base 14 may include a plurality of base panels that are operatively coupled to one another to collectively form the garment base. In such examples, each base panel includes at least one base layer. In such examples, the plurality of base panels may be operatively coupled to one another in any of a variety of manners, such as via stitching and/or via adhesive bonding. Each base layer may be formed of any of a variety of materials. As examples, each base layer may be at least partially formed of a natural fiber, cotton, a synthetic fiber, polyester, nylon, Spandex™ fabric, and/or combinations thereof.

In some examples, portions of footprint perimeter 52 of second absorbent layer 44 and footprint perimeter 54 of first absorbent layer 42 are substantially collinear, and/or follow the same contour as each other. For example, as seen in FIGS. 5-6, portions of footprint perimeters 52, 54 may be collinear along a portion of garment apertures 62, and/or portions of footprint perimeters 52, 54 may follow portions of the contours of garment apertures 62, or other contours of garment 10. In the example of FIGS. 5-6, assembly perimeter 74 of the overall fluid retention assembly 20 is defined by footprint perimeter 54 of first absorbent layer 42, though right and left lateral-edge portions 70, 72 of footprint perimeter 52 of second absorbent layer 44 also are substantially collinear with assembly perimeter 74 (and footprint perimeter 54 of first absorbent layer 42 in in these regions). In contrast, superior edge region 80 and opposite edge region 68 of footprint perimeter 52 of second absorbent layer are not collinear with assembly perimeter 74 or footprint perimeter 54 of first absorbent layer 42.

Figure 7:
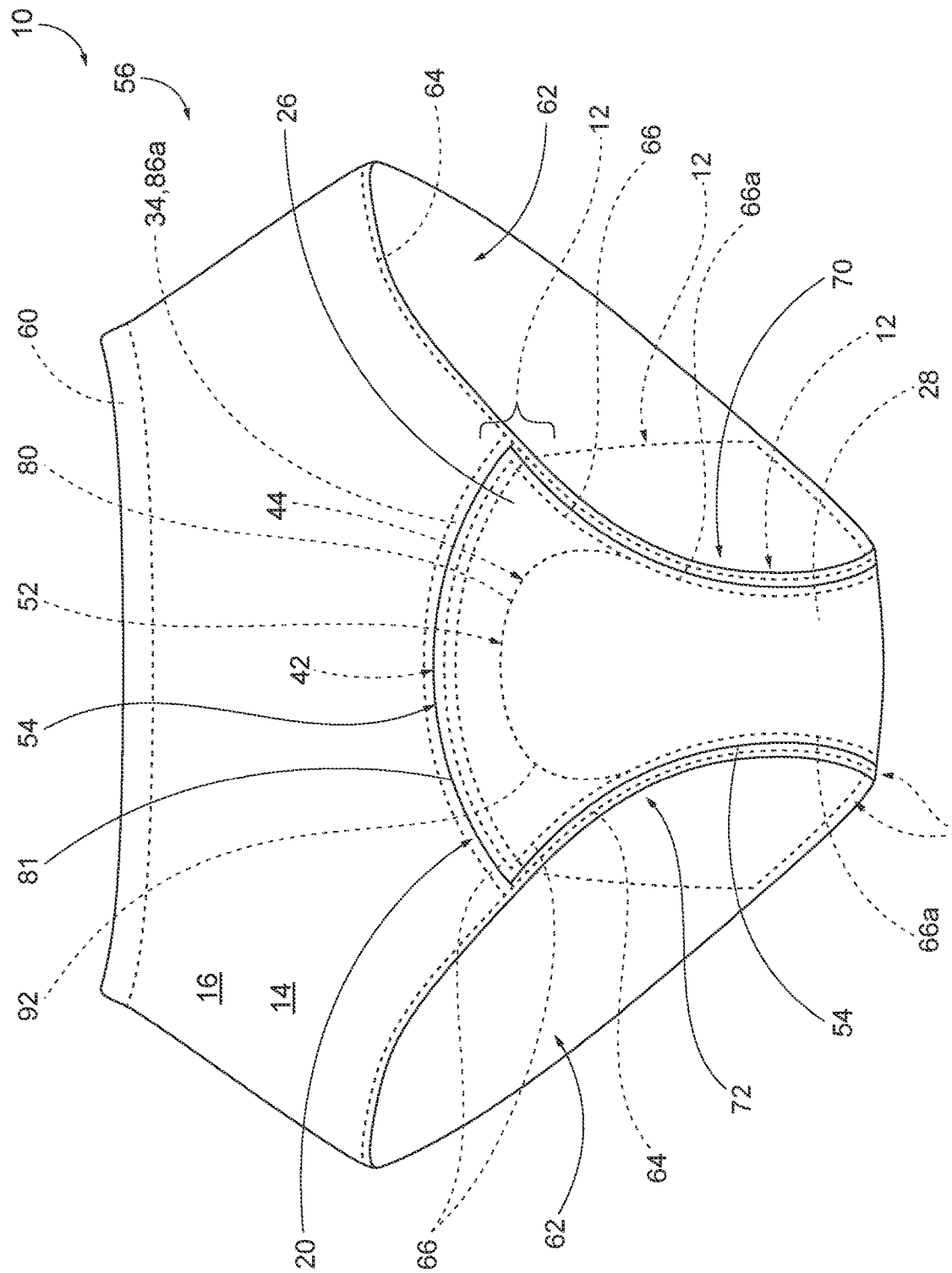
FIG. 7 is a front elevation view of an example of a garment including a fluid retention assembly, shown inside-out.
Figure 8:
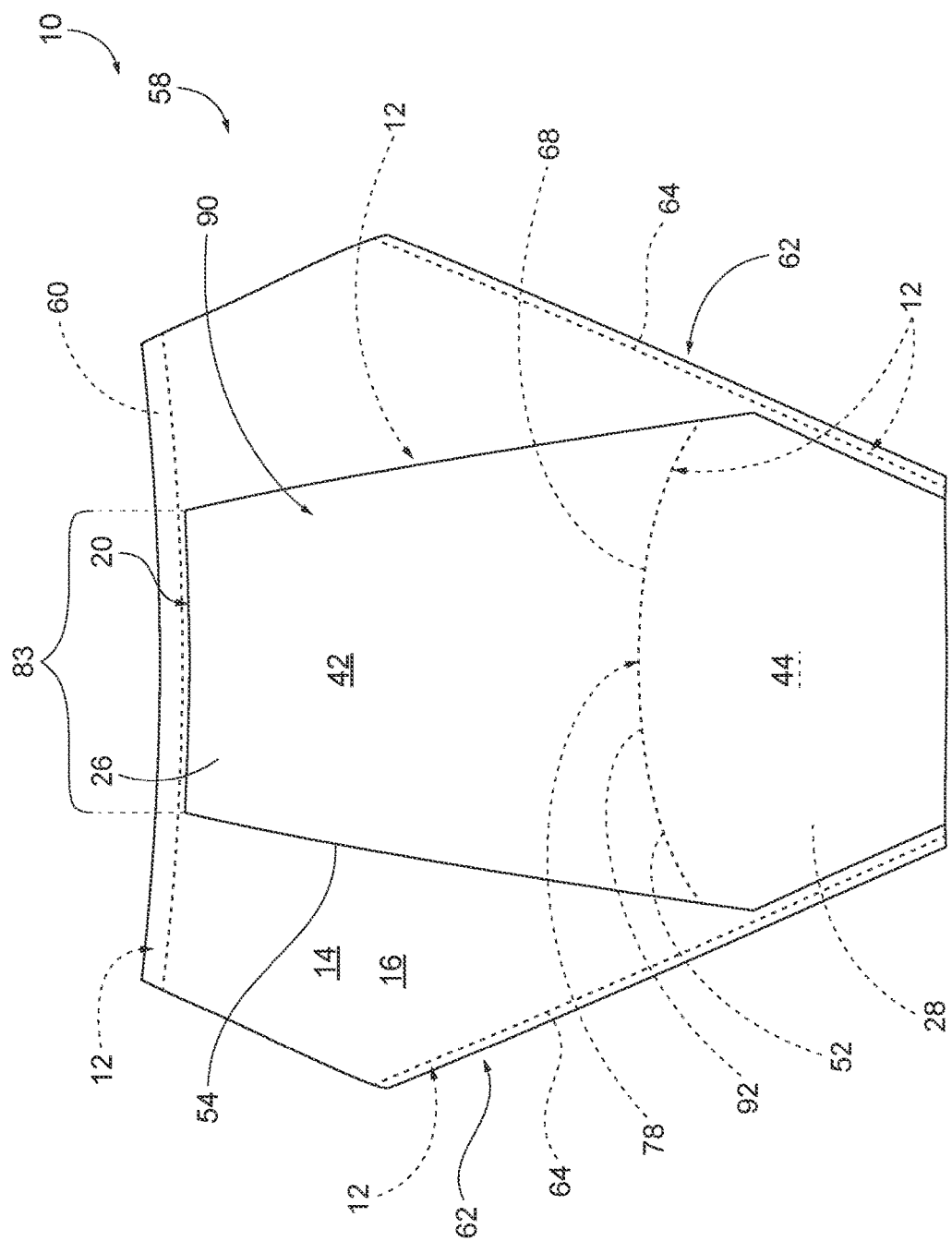
FIG. 8 is a rear elevation view of an example of a garment including a fluid retention assembly, shown inside-out.
Figure 9:
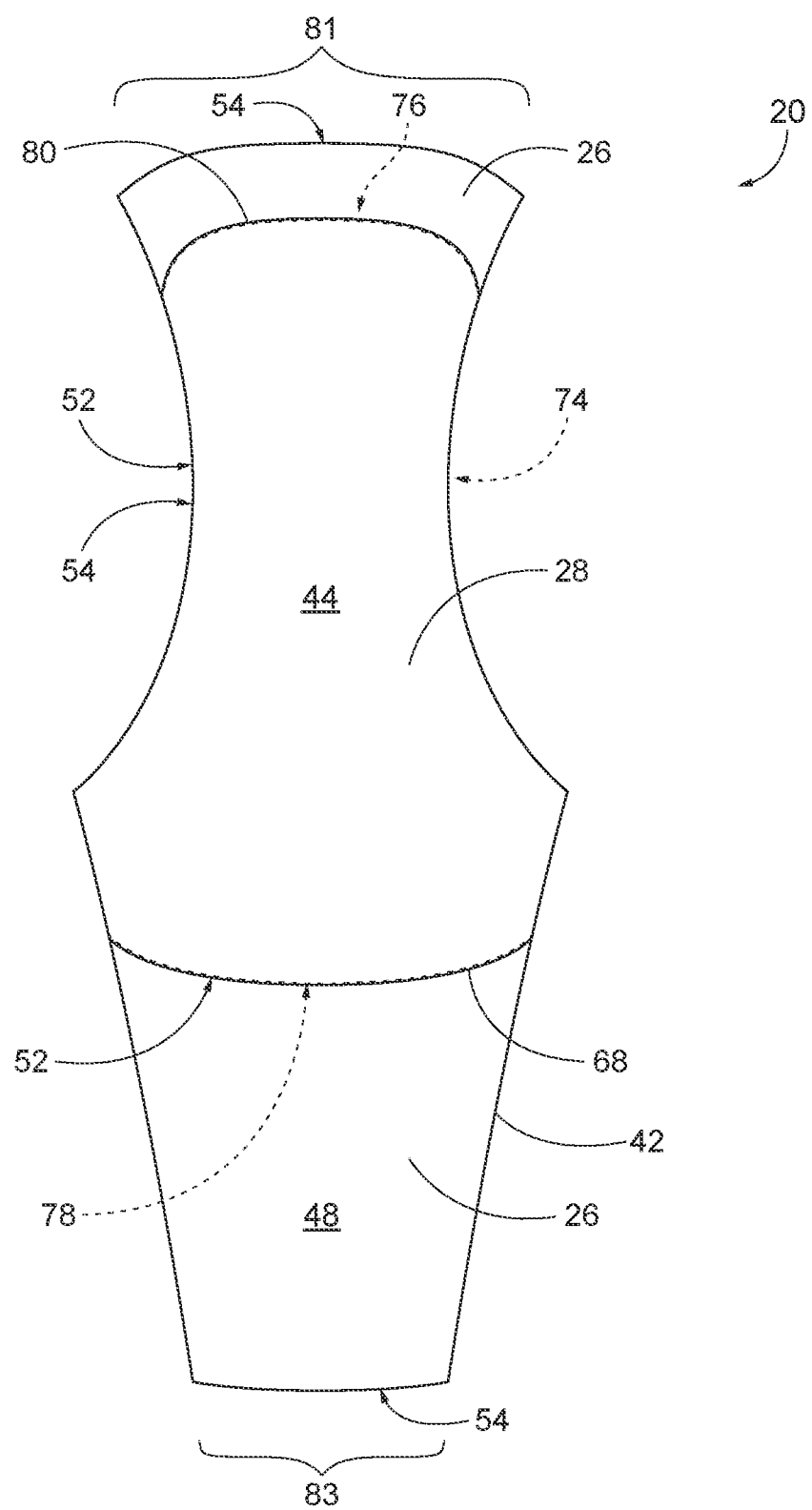
FIG. 9 is a top plan view of an example of fluid retention zones of a fluid retention assembly.

FIGS. 7-9 illustrate another example of garment 10 and fluid retention assembly 20. FIG. 7 is a front (e.g., anterior side) elevation view of another example of garment 10 shown inside-out (e.g., viewing interior side 16 of garment base 14), FIG. 8 is a rear (e.g., posterior side) elevation view of garment 10 from FIG. 7, also shown inside-out, and FIG. 9 is a top plan view of another example of fluid retention assembly 20 from garment 10 of FIGS. 7-8, shown on its own and laid flat for clarity. FIG. 9 illustrates only an example of first fluid-retention zone 26 and second fluid-retention zone 28, without other potential layers of fluid retention assembly 20, to more clearly illustrate the example of fluid retention zones 26, 28. While FIG. 5 illustrates an example of fluid retention assembly 20 extending superiorly to waistband region 60 on anterior side 56 of garment 10 but not on posterior side 58 of garment 10, FIGS. 7-8 illustrate an example in which fluid retention assembly 20 (e.g., first absorbent layer 42) extends superiorly to waistband region 60 on posterior side 58 of garment 10 (FIG. 8), but not on anterior side 56 (FIG. 7). In other examples of garment 10, fluid retention assembly 20 extends superiorly to waistband region 60 on both anterior side 56 and posterior side 58 of garment 10, or on neither anterior side 56 nor posterior side 58 of garment 10.

In the examples of FIGS. 5, 7, and 8, portions of first absorbent layer 42 and second absorbent layer 44 extend laterally to one or more garment apertures 62. For example, in FIG. 5, second absorbent layer 44, and thus second fluid-retention zone 28, extends laterally to garment apertures 62 in the form of left and right leg openings. As used herein, an element is said to "extend laterally to" another element even if there is a small gap or space between the elements, such due to a seam allowance, a bonded region 12, or an edge reinforcing strip 64. As also shown in FIG. 5, first absorbent layer 42 may extend laterally to the leg openings in areas of footprint perimeter 54 of first absorbent layer 42 that are substantially collinear with footprint perimeter 52 of second absorbent layer 44, while other areas of first absorbent layer 42 do not. For example, an angled portion 90 of first absorbent layer 42 may angle medially away from the leg openings as first fluid-retention zone 26 extends superiorly to or towards waistband region 60 on anterior side 56 of garment 10. In the example of FIGS. 7-8, first absorbent layer 42 and second absorbent layer 44 extend laterally to garment apertures 62 on anterior side 56 of garment 10 (FIG. 7), while on posterior side 58 of the garment (FIG. 8), second absorbent layer 44 extends laterally to the leg openings; and another example of angled portion 90 of first absorbent layer 42 angles medially from the leg openings as first fluid-retention zone 26 extends superiorly to or towards waistband region 60. Thus, angled portions 90 of first absorbent layer 42 are spaced away from garment apertures 62 (e.g., the leg openings) in these examples.

As best seen in FIGS. 5 and 7, at least a portion of first absorbent layer 42 and/or second absorbent layer 44 may substantially follow a contour of at least one garment aperture 62. Additionally or alternatively, at least a portion of first absorbent layer 42 and/or second absorbent layer 44 may substantially follow a contour of edge reinforcing strip 64 bonded to garment base 14. Similarly, at least a portion of first absorbent layer 42 may not follow a contour of at least one garment aperture 62, such as angled portions 90 shown in FIGS. 5 and 8. Additionally or alternatively, at least a portion of second absorbent layer 44 may not follow the contour of one or more garment apertures 62, such as curved portions 92 of second absorbent layer 44 shown in FIGS. 7 and 8.

Bonding fluid retention assembly 20 to garment base 14 via adhesive bonds 34 may include bonding via one or more internal peripheral bonds 66 and/or one or more external peripheral bonds 86. The bonding of fluid retention assembly 20 as described herein may enable fluid retention assembly 20 to be incorporated into a wide range of types of garments 10. For example, several prior art absorbent garments include an absorbent pad that is attached to the garment via material that at least partially defines leg openings of the garment, and/or that otherwise necessarily extends adjacent to the leg openings because they rely on the leg openings for positioning and constructional support. By contrast, utilizing adhesive bonds 34 such as internal peripheral bonds 66 and/or external peripheral bonds 86 as disclosed herein may enable fluid retention assembly 20 to be positioned at any desired location within garment 10, such as at a location that is not immediately adjacent to a leg opening or other garment aperture 62. As a result, the constructions disclosed herein are applicable not only to garments 10 in the form of undergarments such as briefs or panties, but also to examples of garments such as trunks, men's underwear, or pants and shorts in which the crotch region is not immediately adjacent to a terminal edge of the garment, or upper body garments or other garments in which it may be desirable to space a fluid retention assembly away from any garment aperture. Accordingly, the shape and/or form of fluid retention assembly 20 itself is not substantially constrained and/or determined by a shape and/or dimension of garment 10 and/or of garment base 14, or by the size or positions of any garment apertures 62. For example, presently disclosed fluid retention assemblies 20 may be readily included in garments configured for urinary incontinence for wearers with male genitalia because the fluid retention assemblies may be positioned in locations of garments 10 even where there is no leg opening to hold on to, while still enabling absorbency on the front side of the garment. Disclosed fluid retention assemblies 20 also may be configured for inclusion in garments meant to protect against urinary incontinence for wearers with female genitalia.

Fluid retention assembly 20 may be bonded to garment base 14, and/or individual layers of fluid retention assembly 20 may be bonded together via plurality of adhesive bonds 34 within one or more bonded regions 12. Bonded region 12 may be positioned along some or all of assembly perimeter 74 of fluid retention assembly 20, along some or all of footprint perimeter 52 of second absorbent layer 44, along some or all of footprint perimeter 54 of first absorbent layer 42, and/or garment 10 may include one or more bonded regions 12 in other areas of garment 10. In other words, bonded region 12 may extend continuously, at least substantially or fully, around assembly perimeter 74 in some examples. The plurality of adhesive bonds 34 may include a variety of different types of bonds between two or more layers or components of garment 10. For example, and with reference to FIGS. 7 and 10, adhesive bonds 34 may include one or more internal peripheral bonds 66 (e.g., internal peripheral bond 66a, 66b, 66c, and/or 66d) that are positioned between layers of fluid retention assembly 20 and formed around, or along at least a portion of, the periphery, or footprint perimeter 52, 54, of one or more layers. Two or more internal peripheral bonds 66 of disclosed garments 10 may be at least substantially collinear along a portion of or all of the lengths of the respective footprint perimeters 52, 54, in some examples.

Figure 10:
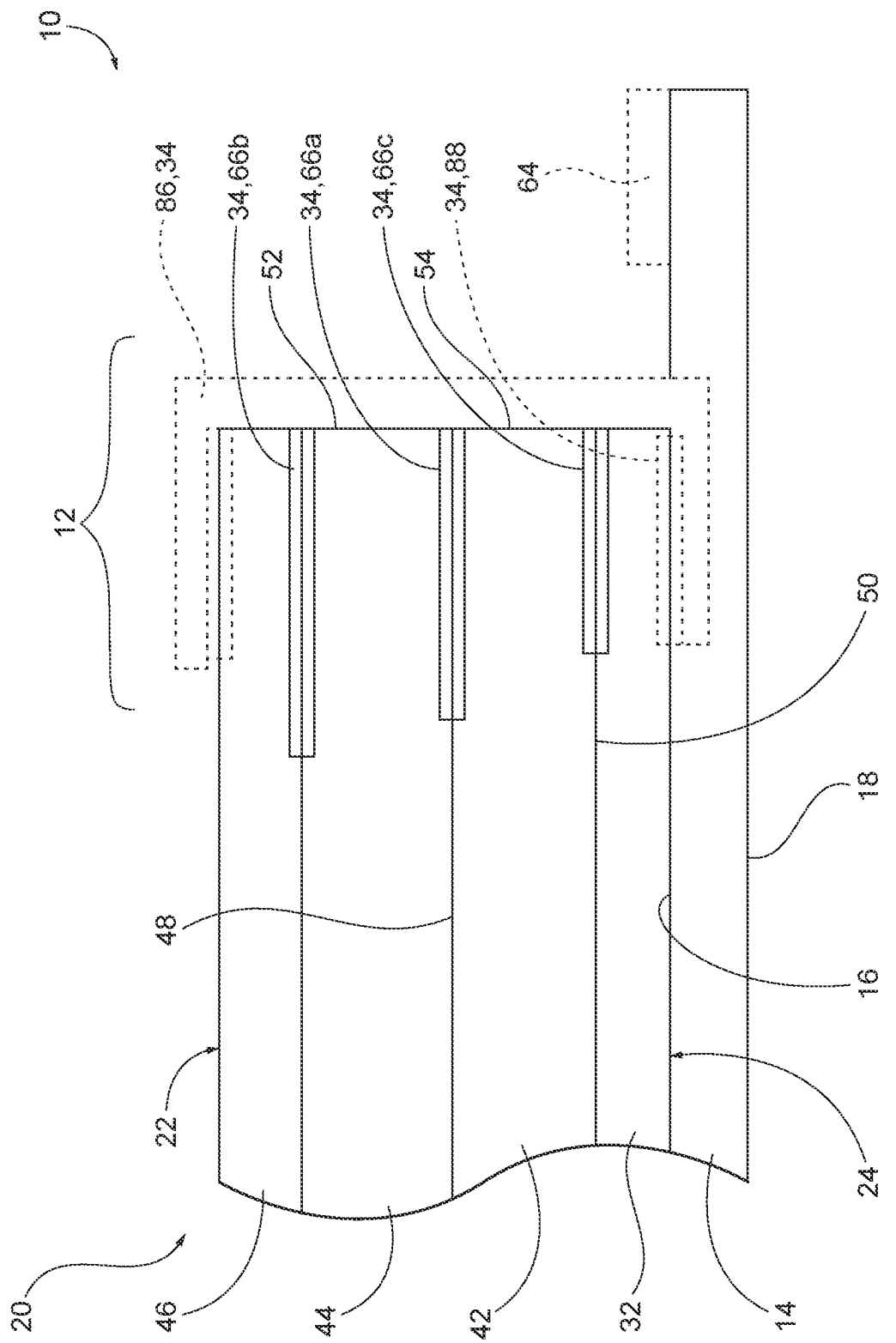
FIG. 10 is a schematic cross-sectional view of an example of a bonded region of a garment including a fluid retention assembly according to the present disclosure.
Figure 11:
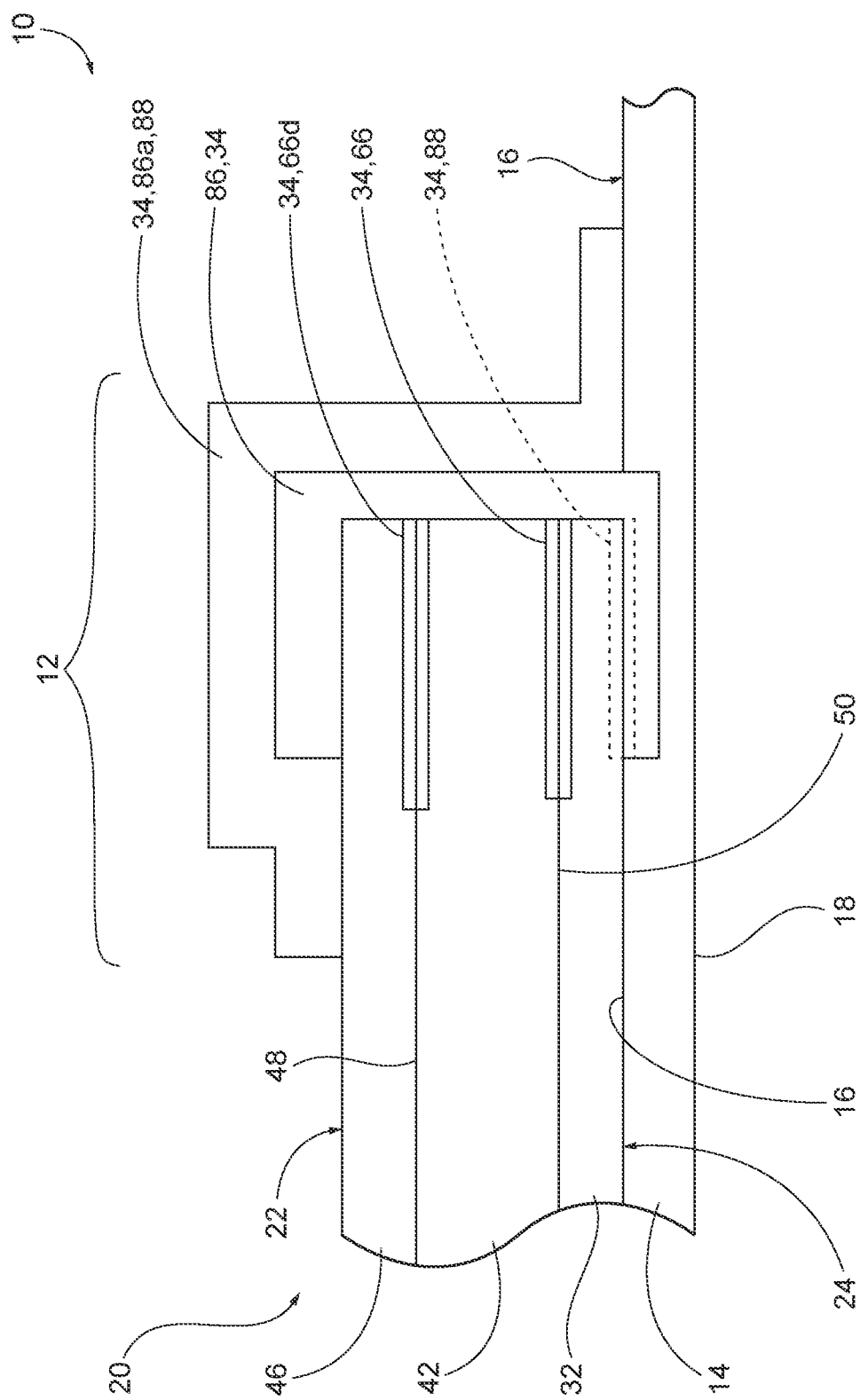
FIG. 11 is a schematic cross-sectional view of an example of a bonded region of a garment including a fluid retention assembly according to the present disclosure.

In FIGS. 10-11, each adhesive bond 34 is indicated by an elongate rectangle that overlaps two or more structures and/or layers of garment base 14 and/or of fluid retention assembly 20. In particular, although FIGS. 10-11 schematically illustrate each adhesive bond 34 as having an extent along the medial-lateral direction, such an illustration is presented for clarity only, and it is to be understood that each adhesive bond 34 and/or the associated adhesive material may exist primarily, solely, and/or at least substantially between, or at an interface between, the structures that are bonded together via the respective adhesive bond. Additionally or alternatively, the associated adhesive material of a given adhesive bond 34 may extend into (e.g., having wicked into) the structures that are bonded together via the adhesive bond. Similarly, it is to be understood that the schematic representations of FIGS. 10-11 are not to scale, and represent the illustrated components as having an exaggerated extent along the medial-lateral direction. The cross-sectional views of FIGS. 10-11 may be understood as being representative of any and/or every location along assembly perimeter 74 of fluid retention assembly 20, footprint perimeter 54 of first absorbent layer 42, and/or footprint perimeter 52 of second absorbent layer 44. In particular, in some examples, the constructions illustrated in the cross-sectional views of FIGS. 10-11 extend fully (or at least substantially fully) around assembly perimeter 74 of fluid retention assembly 20. However, this is not required of all examples of garment 10, and it additionally is within the scope of the present disclosure that the construction of garment 10 may vary at distinct locations along assembly perimeter 74 of fluid retention assembly 20, footprint perimeter 54 of first absorbent layer 42, and/or footprint perimeter 52 of second absorbent layer 44.

Internal peripheral bonds 66 generally are positioned internally within fluid retention assembly 20 such that they are sandwiched between at least two layers of fluid retention assembly 20 or garment 10. For example, an internal peripheral bond 66 may be formed along some or all of footprint perimeter 52 of second absorbent layer 44 to bond second absorbent layer 44 in place with respect to the other components of fluid retention assembly 20. For example, an internal peripheral bond 66a may be used to bond second absorbent layer 44 to first absorbent layer 42 (e.g., inner surface 48 of first absorbent layer 42) along some or all of footprint perimeter 52 of second absorbent layer 44, with internal peripheral bond 66a being positioned between first absorbent layer 42 and second absorbent layer 44 within bonded region 12. In other words, in many examples of garment 10, the entire layer, layers, or features defining second fluid-retention zone 28 are not bonded to other components of fluid retention assembly 20 along the entire footprint or area of second absorbent layer 44, but only along some or all of the periphery, or footprint perimeter 52 of second absorbent layer 44. In other examples, second absorbent layer 44 is bonded to other layers or components of fluid retention assembly 20 in other areas of second fluid-retention zone 28, or even on substantially the entire surface footprint of second absorbent layer 44. Additionally or alternatively, adhesive bonds 34 may include an internal peripheral bond 66b that is configured to bond some or all of footprint perimeter 52 of second absorbent layer 44 to moisture-wicking layer 46 within bonded region 12.

Adhesive bonds 34 may include an internal peripheral bond 66 along some or all of footprint perimeter 54 of first absorbent layer 42. For example, adhesive bonds 34 may include an internal peripheral bond 66c that is configured to bond some or all of footprint perimeter 54 of first absorbent layer 42 (e.g., outer surface 50 of first absorbent layer 42) to moisture-impermeable layer 32 within bonded region 12, thereby bonding first absorbent layer 42 to moisture-impermeable layer 32. In a specific, non-limiting example, and with reference to FIGS. 6 and 10, one respective internal peripheral bond 66 (e.g., internal peripheral bond 66b) may be positioned between moisture-wicking layer 46 and second absorbent layer 44 along the entire footprint perimeter 52 of second absorbent layer 44, while another respective internal peripheral bond 66 (e.g., internal peripheral bond 66a) may be positioned between second absorbent layer 44 and first absorbent layer 42 only along a right and left lateral-edge portion 70, 72 or of second fluid-retention zone 28. Thus, superior edge region 80 of footprint perimeter 52 of second fluid-retention zone 28 may be free from bonding to first absorbent layer 42. One or more other portions of footprint perimeter 52 of second fluid-retention zone 28 may additionally or alternatively be free from bonding to first absorbent layer 42, such as an opposite edge region 68 of footprint perimeter 52 that is opposite superior edge region 80. In other words, in some examples, first absorbent layer 42 and second absorbent layer 44 are not bonded together except along some or all of right and left lateral-edge portions 70, 72 of footprint perimeter 52 of second absorbent layer 44. Opposite edge region 68 may be an inferior edge region in examples where opposite edge region 68 is positioned inferiorly to superior edge region 80 when garment 10 is worn; though in some examples opposite edge region 68 may be positioned superiorly to superior edge region 80 when garment 10 is worn, depending on the positioning and orientation of fluid retention assembly 20 with respect to garment 10.

In some examples, footprint perimeter 52 of second absorbent layer 44 has an anterior edge portion 76 configured to be positioned on anterior side 8 of the wearer when the garment is worn, and a posterior edge portion 78 configured to be positioned on posterior side 9 of the wearer when the garment is worn. Anterior edge portion 76 may correspond to superior edge region 80 of footprint perimeter 52 of second absorbent layer 44, and/or posterior edge portion 78 may correspond to opposite edge region 68 of footprint perimeter 52 of second absorbent layer 44. Though in some examples, the entirety of second fluid-retention zone 28 is positioned on anterior side 56 of garment 10, or the entirety of second fluid-retention zone 28 may be positioned on posterior side 58 of garment 10. Similarly, in some examples of garment 10, second fluid-retention zone 28 is oriented and positioned with respect to the wearer such that anterior edge portion 76 is a different portion of footprint perimeter 52 than superior edge region 80, and/or posterior edge portion 78 is a different portion of footprint perimeter 52 than opposite edge region 68. In examples including anterior edge portion 76 and posterior edge portion 78, said portions 76, 78 may be continuous with right and left lateral-edge portions 70, 72, as best seen in FIG. 6. Additionally or alternatively, right and left lateral-edge portions 70, 72 may be continuous with superior edge region 80 and/or opposite edge region 68. In some examples, first absorbent layer 42 is not bonded to second absorbent layer 44 along anterior edge portion 76 and/or posterior edge portion 78. Additionally or alternatively, in some examples, first absorbent layer 42 is not bonded to second absorbent layer 44 along superior edge region 80 and/or opposite or inferior edge region 68. First fluid-retention zone 26 also may be positioned entirely on anterior side 56 of garment 10, entirely on posterior side 58 of garment 10, or may extend to be positioned on both anterior side 56 and posterior side 58 of garment 10.

In some examples, right and left lateral-edge portions 70, 72 correspond to a portion of assembly perimeter 74 of fluid retention assembly 20, while other regions of footprint perimeter 52 of second absorbent layer 44 (e.g., superior edge region 80 and/or opposite edge region 68) are positioned away from assembly perimeter 74, as shown for example, in FIG. 6. Additionally or alternatively, right lateral-edge portion 70 and/or the left lateral-edge portion 72 may be adjacent to, follow the contour of, and/or be at least partially defined by one or more garment apertures 62. In other words, right lateral-edge portion 70 and left lateral-edge portion 72 may follow the contour of and be positioned adjacent to the leg opening garment apertures 62, as shown in FIG. 7. As used herein, right and left lateral-edge portions 70, 72 may be said to follow the contour of garment apertures 62 without extending around the entire circumference of the garment aperture 62, as shown in FIG. 6.

Additionally or alternatively, adhesive bonds 34 may include a respective internal peripheral bond 66 (e.g., internal peripheral bond 66d) that is configured to bond first absorbent layer 42 to moisture-wicking layer 46 along some or all of footprint perimeter 54 of first absorbent layer 42. For example, while FIG. 10 schematically represents a cross section of bonded region 12 that may correspond to right or left lateral-edge portion 70, 72 of footprint perimeter 52 of second absorbent layer 44, FIG. 11 schematically represents a cross section of bonded region 12 that may correspond to an area where second absorbent layer 44, and thus second fluid-retention zone 28, is not present, such as along superior edge region 81 of footprint perimeter 54 of first absorbent layer 42 (as illustrated in FIG. 7), where first absorbent layer 42 may be bonded directly to moisture-wicking layer 46, rather than sandwiching second absorbent layer 44 between moisture-wicking layer 46 and first absorbent layer 42 as shown in the area represented in FIG. 10.

The plurality of adhesive bonds 34 may include one or more external peripheral bonds 86 positioned on an assembly interior side 22 of fluid retention assembly 20. External peripheral bonds 86 may, in some examples, sandwich the layers of fluid retention assembly 20 such that a portion of external peripheral bond 86 is positioned on assembly interior side 22, and such that a portion of external peripheral bond 86 is positioned on assembly exterior side 24. In some examples, one or more external peripheral bonds 86 are configured to serve as a reinforcement or extra redundancy for one or more internal peripheral bonds 66. Additionally or alternatively, garments 10 may include a respective external peripheral bond 86 (e.g., external peripheral bond 86a in FIGS. 7 and 11) that overlays a portion of fluid retention assembly 20 (e.g., a portion of assembly interior side 22) and a portion of interior side 16 of garment base 14, to reinforce bonding of fluid retention assembly 20 to garment base 14. Such external peripheral bonds 86 may extend along an entire footprint perimeter 54 of first absorbent layer 42, or along just a portion of footprint perimeter 54 of first absorbent layer 42. For example, as best seen in FIG. 7, external peripheral bond 86a may be positioned along superior edge region 81 of footprint perimeter 54, and not along right and left lateral-edge portions 70, 71; though in other examples, external peripheral bond 86a is positioned along right and left lateral-edge portions 70, 72 in addition to or instead of along superior edge region 81. Additionally or alternatively, external peripheral bond 86a may be positioned along an opposite edge region 83 of first absorbent layer 42, which may be positioned on posterior side 58 of garment 10, depending on the size and orientation of fluid retention assembly 20 and the type of garment 10.

Additionally or alternatively, the plurality of adhesive bonds 34 may include one or more assembly-base bonds 88. In some examples, one or more internal peripheral bonds 66 and/or one or more external peripheral bonds 86 serve as an assembly-base bond 88. Each assembly-base bond 88 may be configured to bond at least a portion of fluid retention assembly 20 to at least a portion of garment base 14 (e.g., to one or more base layers of garment base 14). For example, an assembly-base bond 88 may be positioned between moisture-impermeable layer 32 and interior side 16 of garment base 14 to bond fluid retention assembly 20 to garment base 14. In other words, an assembly-base bond 88 may underly fluid retention assembly 20 such that the assembly-base bond 88 is sandwiched between assembly exterior side 24 and interior side 16 of garment base 14. In some examples, one or more assembly-base bonds 88 directly bond at least one base layer of garment base 14 to assembly interior side 22 of fluid retention assembly 20, as shown in FIG. 11. Assembly-base bonds 88 may extend along some or all of assembly perimeter 74 of fluid retention assembly 20, which may correspond to footprint perimeter 54 of first absorbent layer 42. Additionally or alternatively, an assembly-base bond 88 may be positioned between external peripheral bond 86 and garment base 14 to bond fluid retention assembly 20 to garment base 14.

Adhesive bonds 34 may be formed by an adhesive material that is applied to one or both of the garment base 14 and one or more layers of fluid retention assembly 20. Said adhesive material may be a tape (e.g., bonding tape), an elastic tape, a film, an elastic film, a spray-on adhesive, an elastic adhesive, a liquid-curable adhesive, and/or a thermoset adhesive in various non-limiting examples. Additionally or alternatively, the adhesive material used to form one or more adhesive bonds 34 of disclosed garments 10 may be water-resistant, water-repellent, and/or waterproof in some examples. Accordingly, in such examples and as discussed in more detail herein, each such adhesive bond 34 may form a barrier to the passage of moisture and/or bodily fluids, such as to retain such moisture and/or bodily fluids within fluid retention assembly 20 and/or to restrict moisture from entering the fluid retention assembly from an external environment. One or more adhesive bonds 34 may be formed at least partially via a thermocompression process, such as by applying heat and/or pressure to an adhesive material during the manufacture of garment 10 to form one or more adhesive bonds 34. Additional examples of adhesive bonds and bonding techniques that may be used with or incorporated into disclosed garments 10 or fluid retention assemblies 20 are described in U.S. Pat. No. 11,497,263, titled Garments With Moisture Capture Assemblies and Associated Methods, U.S. Pat. No. 10,441,479, titled Absorbent Garment, U.S. patent application Ser. No. 17/877,754, titled Lower Body Garments with an Interior Lining and Related Methods, and U.S. Pat. No. 11,395,774, titled Technologies for Incontinence and Menstrual Garments and Underwear, the complete disclosures of which are incorporated herein by reference.

Figure 12:
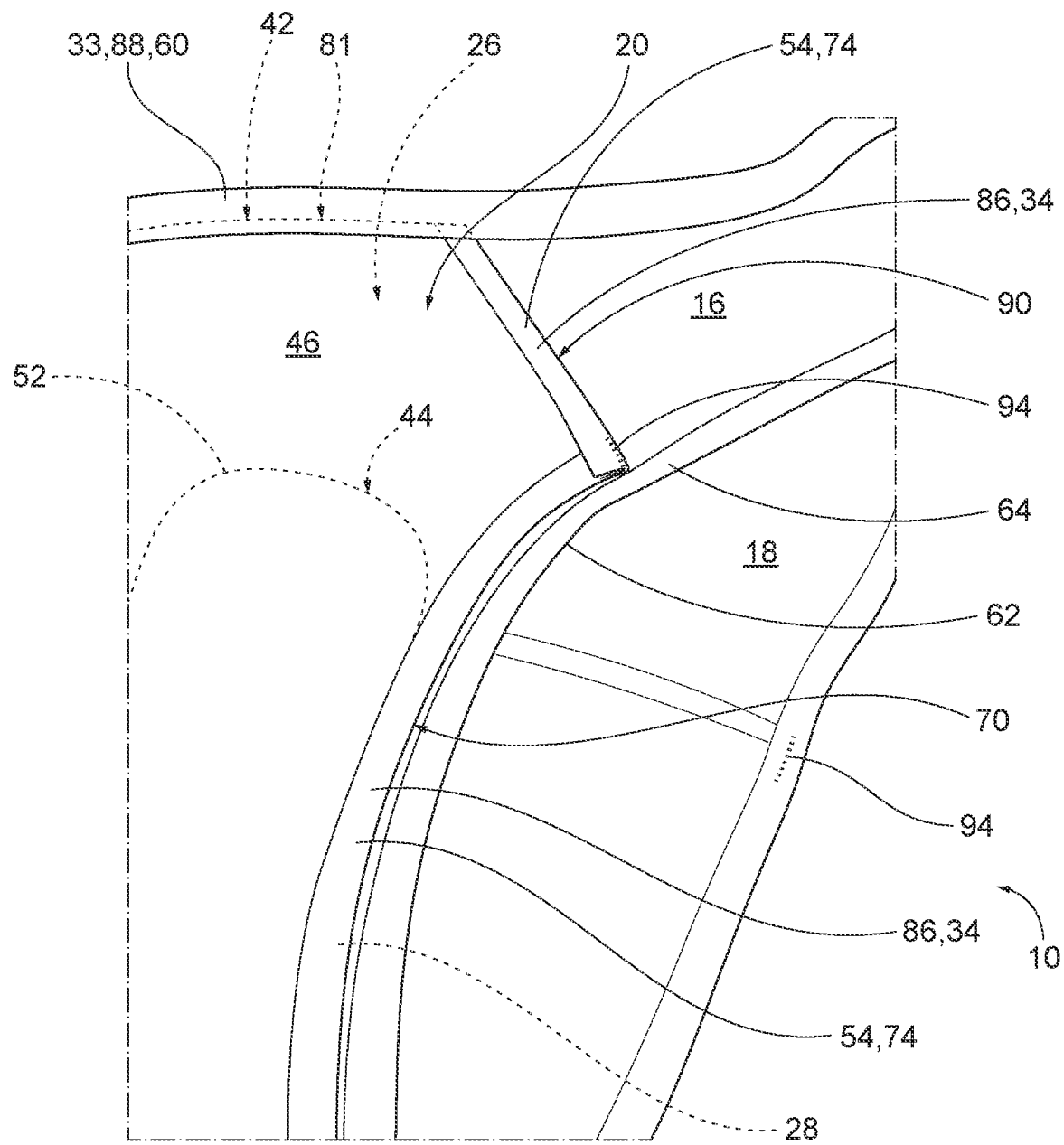
FIG. 12 is a close-up view of a portion of an example of a garment having a fluid retention assembly, shown inside-out.

FIG. 12 illustrates a close-up view of a portion of an example garment 10, shown inside-out. In the example of FIG. 12, fluid retention assembly 20 is bonded to interior side 16 of garment base 14. Right lateral-edge portion 70 of footprint perimeter 54 of first absorbent layer 42 is shown following the contour of garment aperture 62 (e.g., the right leg opening). External peripheral bond 86 may be configured to seal an edge of fluid retention assembly 20 along assembly perimeter 74, and is bonded to interior side 16 of garment base 14 in this example. Right lateral-edge portion 70 of footprint perimeter 54 of first fluid-retention zone 26 is slightly spaced away from edge reinforcement strip 64 that reinforces garment aperture 62, though this portion of footprint perimeter 54 follows the contour of garment aperture 62. Angled portion 90 of footprint perimeter 54 of first fluid-retention zone 26 also includes external peripheral bond 86 sealing the edge of fluid retention assembly 20 and extends to waistband region 60. As shown in FIG. 12, waistband region 60 may partially overlap or overlay superior edge region 81 of footprint perimeter 54 of first absorbent layer 42, and thus may serve as an assembly-based bond 88 that helps bond fluid retention assembly 20 to garment base 14 along superior edge region 81, in this example. In some examples, fluid retention assembly 20 is coupled to garment base 14 entirely by bonding, without any stitching. In some examples, fluid retention assembly 20 is coupled to garment base 14 entirely by stitching, seams, or other coupling mechanisms. In the example of FIG. 12, fluid retention assembly 20 is primarily coupled to garment base 14 via adhesive bonds 34, though this example of FIG. 12 also includes small areas of light stitching or tacking 94, which may be configured to reinforce adhesive bonds 34. For example, bar tack stitching 94 may be added at one or more locations, such as in one or more areas that may be prone to bonding tape delamination over time.

Figure 13:
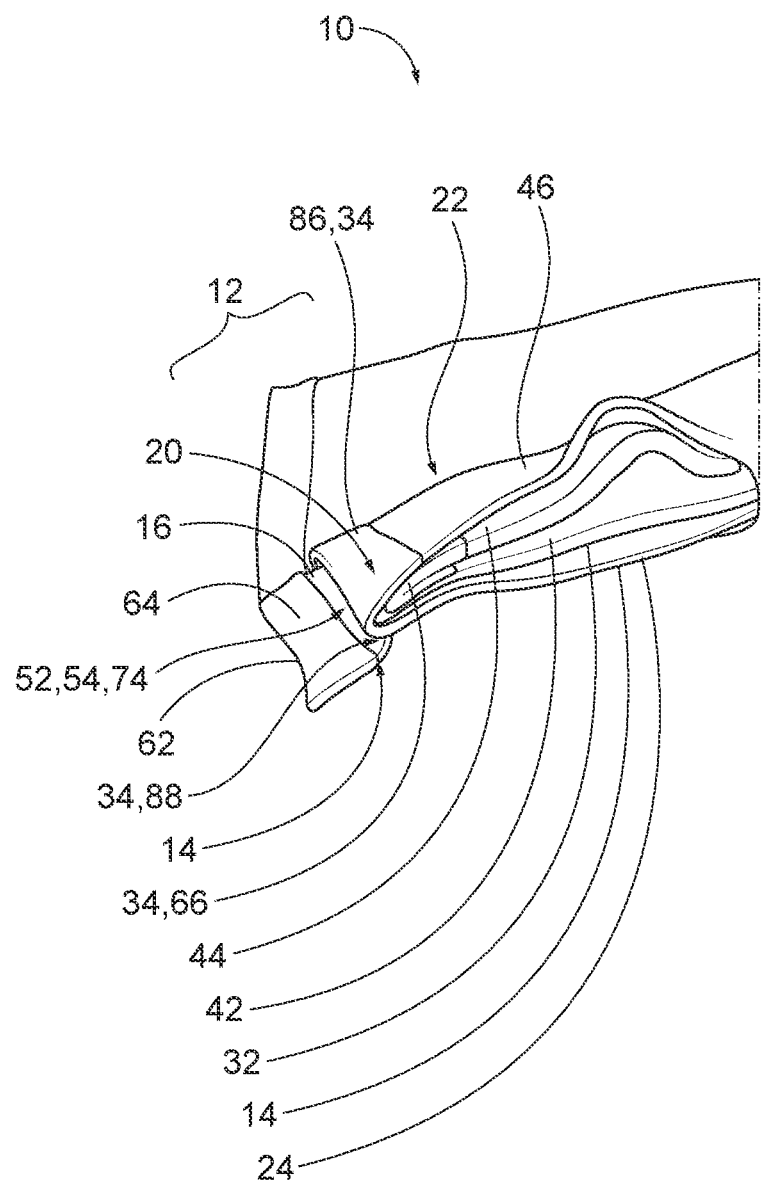
FIG. 13 is a cross-sectional view of a portion of a fluid retention assembly bonded to a garment base according to the present disclosure.

FIG. 13 shows a cross-sectional view of a portion of bonded region 12, showing the layers of fluid retention assembly 20 and bonding of fluid retention assembly 20 to garment base 14, as well as bonding of the layers of fluid retention assembly 20 to each other. The example of garment 10 in FIG. 13 includes an internal peripheral bond 66 that bonds moisture-wicking layer 46 to second absorbent layer 44, an internal peripheral bond 66 that bonds second absorbent layer 44 to first absorbent layer 42, and an internal peripheral bond 66 that bonds first absorbent layer 42 to moisture-impermeable layer 32. External peripheral bond 86 wraps around assembly perimeter 74, such that external peripheral bond 86 is present on both assembly interior side 22 and assembly exterior side 24. As assembly-base bond 88 bonds external peripheral bond 86 to interior side 16 of garment base 14, thereby bonding fluid retention assembly 20 to garment base 14. As visible from FIG. 13, the layers of fluid retention assembly 20 need not be bonded together across the entire layer, and may be bonded together only along footprint perimeter 52 of second absorbent layer 44 and/or footprint perimeter 54 of first absorbent layer 42, each of which may entirely or partially correspond to assembly perimeter 74 of fluid retention assembly 20.

Figure 14:
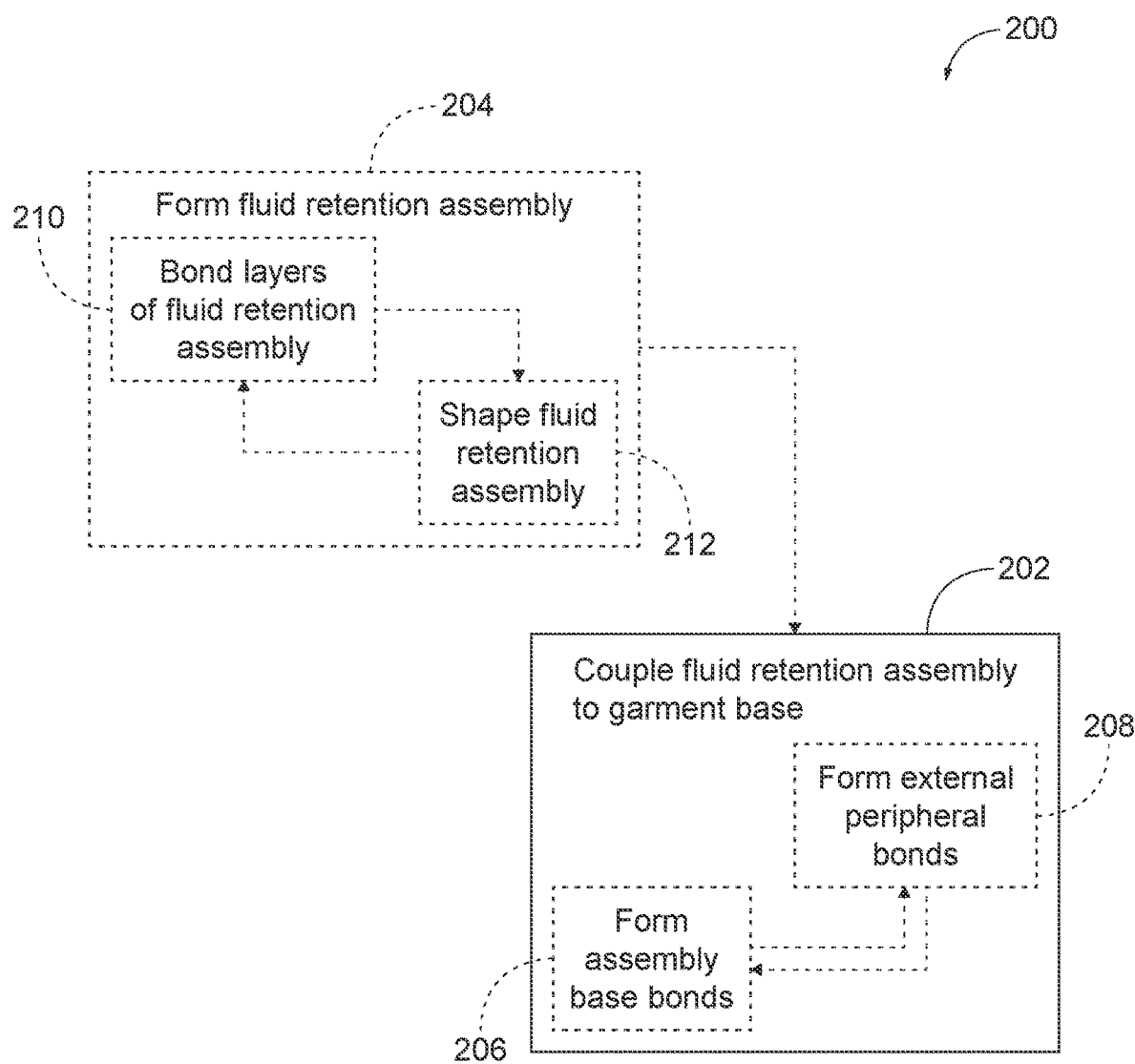
FIG. 14 is a schematic flowchart depicting examples of methods of manufacturing a garment according to the present disclosure.

FIG. 14 schematically provides a flowchart that represents illustrative, non-exclusive examples of methods 200 according to the present disclosure. In FIG. 14, some steps are illustrated in dashed boxes indicating that such steps may be optional or may correspond to an optional version of a method according to the present disclosure. That said, not all methods 200 according to the present disclosure are required to include the steps illustrated in solid boxes. The methods 200 and steps illustrated in FIG. 14 are not limiting, and other methods 200 and steps are within the scope of the present disclosure, including methods 200 having greater than or fewer than the number of steps illustrated, as understood from the discussions herein.

Methods 200 generally include coupling a fluid retention assembly (e.g., fluid retention assembly 20) to a garment base (e.g., garment base 14), at 202. Coupling the fluid retention assembly at 202 may include bonding the fluid retention assembly to the garment base (e.g., via a plurality of adhesive bonds 34), and/or stitching or otherwise coupling the fluid retention assembly to the garment base (e.g., to interior side 16 of garment base 14). In some methods 200, the coupling the fluid retention assembly to the garment base at 202 includes bonding a pre-formed fluid retention assembly to the garment base. In other words, a standalone fluid retention assembly can be made separately and then attached in a desired location on the inside of a garment at 202. In some examples, methods 200 include forming the fluid retention assembly at 204, prior to coupling the fluid retention assembly to the garment base at 202.

Coupling the fluid retention assembly to the garment base at 202 may include forming one or more assembly-base bonds (e.g., one or more assembly-base bonds 88) at 206, to bond at least one base layer of the garment base to at least a portion of the fluid retention assembly. Additionally or alternatively, coupling the fluid retention assembly to the garment base at 202 may include forming one or more external peripheral bonds (e.g., one or more external peripheral bonds 86) at 208.

In methods including forming the fluid retention assembly at 204, said forming the fluid retention assembly may include bonding one or more layers together to form the fluid retention assembly at 210, and/or shaping the fluid retention assembly at 212. For example, one or more layers may be bonded together to form a first absorbent layer (e.g., first absorbent layer 42), one or more layers may be bonded together to form a second absorbent layer (e.g., second absorbent layer 44), and the first and second absorbent layers may be bonded together to form the fluid retention assembly at 204 (e.g., including a first fluid retention zone 26 and a second fluid retention zone 28). Forming the fluid retention assembly at 204 also may include bonding one or more additional layers to the first and second absorbent layers, such as a moisture wicking layer and/or a moisture-impermeable layer. Bonding two or more layers together at 210 may include forming one or more internal peripheral bonds (e.g., one or more internal peripheral bonds 66) between two or more layers of the fluid retention assembly. For example, one or more internal peripheral bonds may be formed at 210 to bond a first absorbent layer, a second absorbent layer, a moisture-impermeable layer, and/or a moisture-wicking layer together. In methods including shaping the fluid retention assembly at 212, said shaping of the fluid retention assembly may be performed before or after the bonding the layers of the fluid retention assembly at 210. For example, shaping the fluid retention assembly at 212 may include cutting the fluid retention assembly to a desired shape, such as by die cutting. Shaping the fluid retention assembly at 212 may be performed to adapt the fluid retention assembly for incorporation with the garment base and/or to adapt the fluid retention assembly for its particular desired use or application with respect to the wearer's body.

Illustrative, non-exclusive examples of inventive subject matter according to the present disclosure are described in the following enumerated paragraphs:

A1. A garment configured to be worn by a wearer, the garment comprising:
- a garment base comprising an interior side and an exterior side, wherein the interior side faces the wearer when the garment is worn by the wearer, and wherein the exterior side faces outwardly away from the wearer when the garment is worn by the wearer; and
- a fluid retention assembly coupled to the interior side of the garment base, wherein the fluid retention assembly comprises:
  - an assembly interior side that faces the wearer when the garment is worn by the wearer;
  - an assembly exterior side that faces outwardly away from the wearer when the garment is worn by the wearer, wherein the assembly exterior side faces the interior side of the garment base;
  - a first fluid-retention zone configured to absorb fluid excreted from the wearer when the garment is worn;
  - a second fluid-retention zone configured to absorb fluid excreted from the wearer when the garment is worn, wherein the second fluid-retention zone has a greater absorbency per unit area than the first fluid-retention zone; and
  - a moisture-impermeable layer positioned with respect to the garment base such that the moisture-impermeable layer separates the interior side of the garment base from the first fluid-retention zone and from the second fluid-retention zone, such that the moisture-impermeable layer is configured to restrict and/or at least substantially prevent fluid from exiting the fluid retention assembly to the exterior side of the garment base.

A2. The garment of paragraph A1, further comprising a bonded region, wherein the fluid retention assembly is bonded to the interior side of the garment base within the bonded region, via a plurality of adhesive bonds formed within the bonded region.

A3. The garment of any of paragraphs A1-A2, wherein the first fluid-retention zone is thinner than the second fluid-retention zone.

A3.1. The garment of paragraph A3, wherein the fluid-retention assembly tapers in thickness between the first fluid-retention zone and the second fluid-retention zone.

A4. The garment of any of paragraphs A1-A3.1, wherein the first fluid-retention zone comprises a first absorbent layer, and wherein the second fluid-retention zone comprises the first absorbent layer and a second absorbent layer overlapped with the first absorbent layer.

A4.1. The garment of paragraph A4, wherein the second absorbent layer overlays a first portion of the first absorbent layer, such that the first portion of the first absorbent layer is sandwiched between the second absorbent layer and the assembly exterior side.

A4.2. The garment of paragraph A4, wherein the second absorbent layer underlies a first portion of the first absorbent layer, such that the second absorbent layer is sandwiched between the first portion of the first absorbent layer and the assembly exterior side.

A4.3. The garment of any of paragraphs A4-A4.2, wherein the first fluid-retention zone comprises a second portion that is not overlapped by the second absorbent layer.

A4.4. The garment of any of paragraphs A4-A4.3, wherein the second absorbent layer is thicker or thinner than the first absorbent layer.

A4.5. The garment of any of paragraphs A4-A4.4, wherein the first absorbent layer comprises a same or a different material than the second absorbent layer.

A4.6. The garment of any of paragraphs A4-A4.5, wherein the first absorbent layer and/or the second absorbent layer comprises polyester nylon.

A4.7. The garment of any of paragraphs A4-A4.6, wherein the first absorbent layer has a first footprint, and wherein the second absorbent layer has a second footprint that is smaller than the first footprint.

A5. The garment of any of paragraphs A1-A4.7, wherein the fluid retention assembly further comprises a moisture-wicking layer that defines the assembly interior side of the fluid retention assembly.

A5.1. The garment of paragraph A5, wherein the moisture-wicking layer comprises cotton, carbon cotton, carbon-cotton spandex, and/or a synthetic fiber fabric.

A5.2. The garment of paragraphs A5 or A5.1, wherein the moisture-wicking layer is configured to be quick-drying, odor-fighting, and/or anti-microbial.

A6. The garment of any of paragraphs A1-A5.2, wherein the moisture-impermeable layer defines the assembly exterior side of the fluid retention assembly.

A7. The garment of any of paragraphs A1-A5.2, wherein the assembly exterior side of the fluid retention assembly is defined by an external layer configured to sandwich the moisture-impermeable layer between the external layer and the first fluid-retention zone and the second fluid-retention zone.

A8. The garment of any of paragraphs A1-A7, wherein the moisture-impermeable layer comprises a coating or treatment applied to an outer surface of the first fluid-retention zone and the second fluid-retention zone, wherein the outer surface is configured to face away from the wearer when the garment is worn by the wearer.

A9. The garment of any of paragraphs A1-A8, wherein the moisture-impermeable layer comprises a leak-resistant or waterproof fabric or other moisture-barrier material, a moisture-barrier layer, a moisture-barrier film, a moisture-barrier membrane, a waterproof, water-resistant, or water-repellant treatment, and/or a waterproof, water-resistant, or water-repellant coating.

A10. The garment of any of paragraphs A1-A9, wherein the first fluid-retention zone and the second fluid-retention zone are sandwiched between a/the moisture-wicking layer of the fluid retention assembly and the moisture-impermeable layer.

A11. The garment of any of paragraphs A1-A10, wherein the garment comprises a plurality of fluid retention assemblies spaced apart from one another.

A12. The garment of any of paragraphs A1-A11, wherein the fluid retention assembly is positioned in a region of the garment that is configured to be positioned on, adjacent to, and/or around the wearer's pelvic region, armpit region, bra line regions, torso region, back, shoulders, buttocks, legs, arms, chest, neck, nipples, and/or breast region when the garment is worn by the wearer.

A13. The garment of any of paragraphs A1-A12, wherein the second fluid-retention zone comprises a plurality of second fluid-retention zones.

A13.1. The garment of paragraph A13, wherein each respective second fluid-retention zone of the plurality of second fluid-retention zones is formed by a region of overlap between a respective second absorbent layer and a respective portion of a/the first absorbent layer.

A14. The garment of any of paragraphs A1-A13, further comprising one or more additional fluid-retention zones formed by one or more regions of overlap between a portion of one or more second absorbent layers with one or more additional absorbent layers.

A15. The garment of any of paragraphs A1-A14, wherein the second fluid-retention zone extends superiorly to a lesser extent than does the first fluid-retention zone on an anterior side of the garment.

A16. The garment of any of paragraphs A1-A15, wherein the second fluid-retention zone extends superiorly to a lesser extent than does the first fluid-retention zone on a posterior side of the garment.

A17. The garment of any of paragraphs A1-A16, wherein the second fluid-retention zone extends laterally to a lesser extent than does the first fluid-retention zone.

A18. The garment of any of paragraphs A1-A17, wherein the garment includes a waistband region; and optionally wherein the garment base at least partially defines the waistband region.

A18.1. The garment of paragraph A18, wherein the first fluid-retention zone and/or the second fluid-retention zone extends to the waistband region on an/the anterior side of the garment and/or a/the posterior side of the garment.

A18.2. The garment of paragraph A18 or A18.1, wherein the first fluid-retention zone and/or the second fluid-retention zone do not extend to the waistband region on an/the anterior side of the garment and/or a/the posterior side of the garment.

A18.3. The garment of any of paragraphs A18-A18.2, wherein one of a/the first absorbent layer and a/the second absorbent layer extends closer to the waistband region than the other of the first absorbent layer and the second absorbent layer on an/the anterior side of the garment and/or a/the posterior side of the garment.

A19. The garment of any of paragraphs A1-A18.3, wherein the garment defines one or more garment apertures; and optionally wherein the garment base at least partially defines the one or more garment apertures.

A19.1. The garment of paragraph A19, wherein at least one garment aperture of the one or more garment apertures defines a leg opening that is configured to receive a leg of the wearer when the garment is worn by the wearer.

A19.2. The garment of paragraph A19 or A19.1, wherein at least one garment aperture of the one or more garment apertures defines an arm opening that is configured to receive an arm of the wearer when the garment is worn by the wearer.

A19.3. The garment of any of paragraphs A19-A19.2, further comprising an edge reinforcing strip positioned adjacent to at least one garment aperture of the one or more garment apertures.

A19.3.1. The garment of paragraph A19.3, wherein the edge reinforcing strip is bonded to the garment base with at least one adhesive bond of a/the plurality of adhesive bonds.

A19.3.2. The garment of paragraph A19.3 or A19.3.1, wherein the edge reinforcing strip at least partially defines the at least one garment aperture; and optionally wherein the edge reinforcing strip at least partially defines a/the leg opening.

A19.3.3. The garment of any of paragraphs A19.3-A19.3.2, wherein the edge reinforcing strip is an elastic strip.

A19.4. The garment of any of paragraphs A19-A19.3.3, wherein the first fluid-retention zone and/or the second fluid-retention zone extend laterally to at least one garment aperture of the one or more garment apertures.

A19.5. The garment of any of paragraphs A19-A19.4, wherein the first fluid-retention zone and/or the second fluid-retention zone does not extend to the one or more garment apertures.

A19.6. The garment of any of paragraphs 194-A19.5, wherein at least a portion of the first fluid-retention zone or a/the first absorbent layer substantially follows a contour of at least one garment aperture of the one or more garment apertures.

A19.7. The garment of any of paragraphs A19-A19.6, wherein at least a portion of the first fluid-retention zone or a/the first absorbent layer substantially follows a contour of an/the edge reinforcing strip bonded to the garment base.

A19.8. The garment of any of paragraphs A19-A19.7, wherein at least a portion of the second fluid-retention zone substantially follows a contour of at least one garment aperture of the one or more garment apertures.

A19.9. The garment of any of paragraphs A19-A19.8, wherein at least a portion of the second fluid-retention zone substantially follows a contour of an/the edge reinforcing strip bonded to the garment base.

A19.10. The garment of any of paragraphs A19-A19.9, wherein at least a portion of the first fluid-retention zone does not follow a contour of at least one garment aperture of the one or more garment apertures.

A19.11. The garment of any of paragraphs A19-A19.10, wherein at least a portion of the second fluid-retention zone does not follow a contour of at least one garment aperture of the one or more garment apertures.

A20. The garment of any of paragraphs A1-A19.11, wherein a/the plurality of adhesive bonds comprises an internal peripheral bond along a perimeter of the second fluid-retention zone.

A20.1. The garment of paragraph A20, wherein the internal peripheral bond along the perimeter of the second fluid-retention zone bonds the second fluid-retention zone to a/the moisture-wicking layer of the fluid retention assembly.

A20.2. The garment of paragraph A20 or A20.1, wherein at least a portion of the perimeter of a/the second absorbent layer is not bonded to a/the first absorbent layer.

A20.3. The garment of any of paragraphs A20-A20.2, wherein the internal peripheral bond extends along a left lateral-edge portion and a right lateral-edge portion of the perimeter of the second fluid-retention zone.

A20.3.1. The garment of paragraph A20.3, wherein the left lateral-edge portion and the right lateral-edge portion correspond to an assembly perimeter of the fluid retention assembly.

A20.3.2. The garment of paragraph A20.3 or A20.3.1, wherein the right lateral-edge portion and/or the left lateral-edge portion is adjacent to, follows the contour of, and/or is at least partially defined by a/the garment aperture of a/the one or more garment apertures.

A20.3.3. The garment of any of paragraphs A20.3-A20.3.2, wherein a/the first absorbent layer and a/the second absorbent layer are not bonded together except along some or all of the left and right lateral-edge portions.

A20.4. The garment of any of paragraphs A20-A20.3.3, wherein the internal peripheral bond along the perimeter of the second fluid-retention zone comprises an anterior edge portion continuous with a/the left lateral-edge portion and a/the right lateral-edge portion.

A20.4.1. The garment of paragraph A20.4, wherein the anterior edge portion is configured to be positioned on an anterior side of the wearer when the garment is worn by the wearer.

A20.4.2. The garment of paragraph A20.4 or A20.4.1, wherein a/the second absorbent layer is not bonded to a/the first absorbent layer along the anterior edge portion of the perimeter of the second fluid-retention zone.

A20.5. The garment of any of paragraphs A20-A20.4.2, wherein the internal peripheral bond along the perimeter of the second fluid-retention zone comprises a posterior edge portion continuous with a/the left lateral-edge portion and a/the right lateral-edge portion.

A20.5.1. The garment of paragraph A20.5, wherein the posterior edge portion is configured to be positioned on a posterior side of the wearer when the garment is worn by the wearer.

A20.5.2. The garment of paragraph A20.5 or A20.5.1, wherein a/the second absorbent layer is not bonded to a/the first absorbent layer along the posterior edge portion of the perimeter of the second fluid-retention zone.

A20.6. The garment of any of paragraphs A20-A20.5.2, wherein the perimeter of the second fluid-retention zone comprises a superior edge portion and an inferior edge portion, each being continuous with a/the left lateral-edge portion and a/the right lateral-edge portion, and wherein the inferior edge portion is configured to be positioned inferior to the superior edge portion when the garment is worn by the wearer.

A20.6.1. The garment of paragraph A20.6, wherein a/the second absorbent layer is not bonded to a/the first absorbent layer along the superior edge portion of the perimeter of the second fluid-retention zone or along the inferior edge portion of the perimeter of the second fluid-retention zone.

A20.7. The garment of any of paragraphs A20-A20.6.1, wherein the internal peripheral bond along the perimeter of the second fluid-retention zone is positioned internally within the fluid retention assembly such that the internal peripheral bond is between at least two layers of the garment or the fluid retention assembly.

A21. The garment of any of paragraphs A1-A20.7, wherein the a/plurality of adhesive bonds comprises an internal peripheral bond along a perimeter of a/the first absorbent layer.

A21.1. The garment of paragraph A21, wherein the internal peripheral bond along the perimeter of the first absorbent layer bonds the first absorbent layer to the moisture-impermeable layer.

A21.2. The garment of paragraph A21 or A21.1, wherein the internal peripheral bond along the perimeter of the first absorbent layer bonds the first absorbent layer to the garment base.

A21.3. The garment of any of paragraphs A21-A21.2, wherein the internal peripheral bond along the perimeter of the first absorbent layer bonds the first absorbent layer to a/the moisture-wicking layer.

A21.4. The garment of any of paragraphs A21-A21.3, wherein the internal peripheral bond along the perimeter of the first absorbent layer bonds to a/the second absorbent layer only along a/the right lateral-edge region and a/the left lateral-edge region of the second fluid-retention zone.

A21.5. The garment of any of paragraphs A21-A21.4, wherein the internal peripheral bond along the perimeter of the first absorbent layer is positioned internally within the fluid retention assembly such that the internal peripheral bond is between at least two layers of the garment.

A21.6. The garment of any of paragraphs A21-A21.5, wherein the internal peripheral bond along the perimeter of the first absorbent layer is at least substantially collinear with a portion of a/the internal peripheral bond along a/the perimeter of a/the second absorbent layer.

A22. The garment of any of paragraphs A1-A21.6, wherein a/the plurality of adhesive bonds includes an external peripheral bond positioned on the assembly interior side of the fluid retention assembly.

A23. The garment of any of paragraphs A1-A22, wherein a/the plurality of adhesive bonds includes one or more assembly-base bonds; and wherein each assembly-base bond of the one or more assembly-base bonds operates to bond at least a portion of the fluid retention assembly to at least a portion of the garment base.

A23.1. The garment of paragraph A23, wherein the one or more assembly-base bonds includes one or both of an/the internal peripheral bond and an/the external peripheral bond.

A24. The garment of any of paragraphs A1-A23.1, wherein one or more adhesive bonds of a/the plurality of adhesive bonds are formed by an adhesive material that is applied to one or both of the garment base and the fluid retention assembly.

A24.1. The garment of paragraph A24, wherein the adhesive material includes one or more of a tape, an elastic tape, a film, an elastic film, a spray-on adhesive, and a thermoset adhesive.

A24.2. The garment of paragraph A24 or A24.1, wherein the adhesive material is one or more of water-resistant, water-repellent, and waterproof.

A25. The garment of any of paragraphs A1-A24.2, wherein one or more adhesive bonds of a/the plurality of adhesive bonds are formed at least partially via a thermo-compression process.

A26. The garment of any of paragraphs A1-A25, wherein a/the bonded region of the garment extends at least substantially or fully around an/the assembly perimeter of the fluid retention assembly.

A27. The garment of any of paragraphs A1-A26, wherein the garment base includes one or more base layers.

A27.1. The garment of paragraph A27, wherein at least one base layer of the one or more base layers and at least a portion of the fluid retention assembly are bonded to one another via at least one assembly-base bond of a/the one or more assembly-base bonds.

A28. The garment of any of paragraphs A1-A27.1, wherein at least one assembly-base bond of a/the one or more assembly-base bonds directly bonds at least one base layer of the one or more base layers of the garment base to the assembly interior side of the fluid retention assembly.

A29. The garment of any of paragraphs A1-A28, wherein at least one assembly-base bond of a/the one or more assembly-base bonds overlies a portion of the assembly interior side and a portion of the interior side of the garment base.

A30. The garment of any of paragraphs A1-A29, wherein at least one assembly-base bond of a/the one or more assembly-base bonds underlies the fluid retention assembly such that the at least one assembly-base bond is sandwiched between the assembly exterior side and the interior side of the garment base.

A31. The garment of any of paragraphs A1-A30, wherein the garment base includes a plurality of base panels that are operatively coupled to one another.

A32. The garment of any of paragraphs A1-A31, wherein the garment base is at least partially formed of one or more of a natural fiber, cotton, a synthetic fiber, polyester, nylon, Spandex™ fabric, and combinations thereof.

A33. The garment of any of paragraphs A1-A32, wherein the garment is an undergarment.

A34. The garment of any of paragraphs A1-A32, wherein the garment is an outerwear garment.

A35. The garment of any of paragraphs A1-A34, wherein the garment is a short (e.g., a pair of shorts).

A36. The garment of any of paragraphs A1-A35, wherein the garment is an activewear garment.

A37. The garment of any of paragraphs A1-A36, wherein the garment is a top.

A38. The garment of any of paragraphs A1-A37, wherein the garment is configured to be washed and re-worn numerous times.

A39. The garment of any of paragraphs A1-A38, wherein one or more of the fluid retention assembly, a/the first absorbent layer, a/the second absorbent layer, a/the moisture-wicking layer, and the moisture-impermeable layer is at least partially formed of one or more of a natural fiber, cotton, a synthetic fiber, polyester, nylon, Spandex™ fabric, and combinations thereof.

A40. The garment of any of paragraphs A1-A39, wherein the exterior side of the garment base is free from seams along an/the assembly perimeter of the fluid retention assembly.

B1. A method of manufacturing the garment of any of paragraphs A1-A40, the method comprising:
    bonding, with a/the plurality of adhesive bonds, the fluid retention assembly to the garment base.

B2. The method of paragraph B1, wherein the bonding the fluid retention assembly to the garment base includes forming a/the one or more assembly-base bonds to bond at least one base layer of a/the one or more base layers and at least a portion of the fluid retention assembly to one another.

B2.1. The method of paragraph B2, wherein the bonding the fluid retention assembly to the garment base includes forming an/the internal peripheral bond.

B2.2. The method of paragraph B2 or B2.1, wherein the bonding the fluid retention assembly to the garment base includes forming an/the external peripheral bond.

B3. The method of any of paragraphs B1-B2.2, further comprising, prior to the bonding the fluid retention assembly to the garment base, forming the fluid retention assembly.

B3.1. The method of paragraph B3, wherein the forming the fluid retention assembly includes bonding two or more layers of the fluid retention assembly to one another; optionally wherein the two or more layers of the fluid retention assembly include the moisture-impermeable layer, a/the first absorbent layer, a/the second absorbent layer, a/the moisture-wicking layer, and/or an/the external layer.

B3.2. The method of paragraph B3 or B3.1, wherein the forming the fluid retention assembly includes shaping the fluid retention assembly.

B3.2.1. The method of paragraph B3.2 when dependent from paragraph B3.1, wherein the shaping the fluid retention assembly is performed subsequent to the bonding the two or more layers of the fluid retention assembly to one another.

B3.3. The method of any of paragraphs B3-B3.2.1, wherein the forming the fluid retention assembly includes cutting the fluid retention assembly to a desired shape.

B3.3.1. The method of paragraph B3.3, wherein the cutting the fluid retention assembly to the desired shape includes die cutting.

B3.4. The method of any of paragraphs B3-B3.3.1, wherein the forming the fluid retention assembly includes bonding a/the second absorbent layer to a/the first absorbent layer.

B3.5. The method of any of paragraphs B3-B3.4, wherein the forming the fluid retention assembly comprises bonding a/the second absorbent layer to a/the first absorbent layer to form a/the second fluid-retention zone.

C1. A method of manufacturing the garment of any of paragraphs A1-A40, the method comprising:
    coupling the fluid retention assembly to the garment base.

C2. The method of paragraphs C1, further comprising, prior to the coupling the fluid retention assembly to the garment base, forming the fluid retention assembly.

C2.1. The method of paragraph C2, wherein the forming the fluid retention assembly includes bonding two or more layers of the fluid retention assembly to one another; optionally wherein the two or more layers of the fluid retention assembly include the moisture-impermeable layer, a/the first absorbent layer, a/the second absorbent layer, a/the moisture-wicking layer, and/or an/the external layer.

C2.2. The method of paragraph C2 or C2.1, wherein the forming the fluid retention assembly includes shaping the fluid retention assembly.

C2.2.1. The method of paragraph C2.2 when dependent from paragraph C2.1, wherein the shaping the fluid retention assembly is performed subsequent to the bonding the two or more layers of the fluid retention assembly to one another.

C2.3. The method of any of paragraphs C2-C2.2.1, wherein the forming the fluid retention assembly includes cutting the fluid retention assembly to a desired shape.

C2.3.1. The method of paragraph C2.3, wherein the cutting the fluid retention assembly to the desired shape includes die cutting.

C2.4. The method of any of paragraphs C2-C2.3.1, wherein the forming the fluid retention assembly includes bonding a/the second absorbent layer to a/the first absorbent layer.

C2.5. The method of any of paragraphs C2-C2.4, wherein the forming the fluid retention assembly comprises bonding a/the second absorbent layer to a/the first absorbent layer to form a/the second fluid-retention zone.

D1. Use of the garment of any of paragraphs A1-A40 to absorb and retain fluid excretions from the wearer of the garment.

As used herein, the terms "adapted" and "configured" mean that the element, component, or other subject matter is designed and/or intended to perform a given function. Thus, the use of the terms "adapted" and "configured" should not be construed to mean that a given element, component, or other subject matter is simply "capable of" performing a given function but that the element, component, and/or other subject matter is specifically selected, created, implemented, utilized, programmed, and/or designed for the purpose of performing the function. It is also within the scope of the present disclosure that elements, components, and/or other recited subject matter that is recited as being adapted to perform a particular function may additionally or alternatively be described as being configured to perform that function, and vice versa. Similarly, subject matter that is recited as being configured to perform a particular function may additionally or alternatively be described as being operative to perform that function.

As used herein, the term "and/or" placed between a first entity and a second entity means one of (1) the first entity, (2) the second entity, and (3) the first entity and the second entity. Multiple entries listed with "and/or" should be construed in the same manner, i.e., "one or more" of the entities so conjoined. Other entities optionally may be present other than the entities specifically identified by the "and/or" clause, whether related or unrelated to those entities specifically identified. Thus, as a non-limiting example, a reference to "A and/or B," when used in conjunction with open-ended language such as "comprising," may refer, in one example, to A only (optionally including entities other than B); in another example, to B only (optionally including entities other than A); in yet another example, to both A and B (optionally including other entities). These entities may refer to elements, actions, structures, steps, operations, values, and the like.

As used herein, the phrase "at least one," in reference to a list of one or more entities should be understood to mean at least one entity selected from any one or more of the entities in the list of entities, but not necessarily including at least one of each and every entity specifically listed within the list of entities and not excluding any combinations of entities in the list of entities. This definition also allows that entities may optionally be present other than the entities specifically identified within the list of entities to which the phrase "at least one" refers, whether related or unrelated to those entities specifically identified. Thus, as a non-limiting example, "at least one of A and B" (or, equivalently, "at least one of A or B," or, equivalently "at least one of A and/or B") may refer, in one embodiment, to at least one, optionally including more than one, A, with no B present (and optionally including entities other than B); in another embodiment, to at least one, optionally including more than one, B, with no A present (and optionally including entities other than A); in yet another embodiment, to at least one, optionally including more than one, A, and at least one, optionally including more than one, B (and optionally including other entities). In other words, the phrases "at least one," "one or more," and "and/or" are open-ended expressions that are both conjunctive and disjunctive in operation. For example, each of the expressions "at least one of A, B, and C," "at least one of A, B, or C," "one or more of A, B, and C," "one or more of A, B, or C," and "A, B, and/or C" may mean A alone, B alone, C alone, A and B together, A and C together, B and C together, A, B, and C together, and optionally any of the above in combination with at least one other entity.

As used herein, the phrase "at least substantially," when modifying a degree or relationship, includes not only the recited "substantial" degree or relationship, but also the full extent of the recited degree or relationship. A substantial amount of a recited degree or relationship may include at least 75% of the recited degree or relationship. For example, a first component that extends at least substantially around a second component includes a first component that extends around at least 75% of a circumference of the second component and also includes a first component that extends fully circumferentially around the second component.

As used herein, the phrase, "for example," the phrase, "as an example," and/or simply the term "example," when used with reference to one or more components, features, details, structures, embodiments, and/or methods according to the present disclosure, are intended to convey that the described component, feature, detail, structure, embodiment, and/or method is an illustrative, non-exclusive example of components, features, details, structures, embodiments, and/or methods according to the present disclosure. Thus, the described component, feature, detail, structure, embodiment, and/or method is not intended to be limiting, required, or exclusive/exhaustive; and other components, features, details, structures, embodiments, and/or methods, including structurally and/or functionally similar and/or equivalent components, features, details, structures, embodiments, and/or methods, are also within the scope of the present disclosure.

The various disclosed elements of apparatuses disclosed herein are not required to all apparatuses according to the present disclosure, and the present disclosure includes all novel and non-obvious combinations and subcombinations of the various elements disclosed herein. Moreover, one or more of the various elements disclosed herein may define independent inventive subject matter that is separate and apart from the whole of a disclosed apparatus. Accordingly, such inventive subject matter is not required to be associated with the specific apparatuses that are expressly disclosed herein, and such inventive subject matter may find utility in apparatuses and/or methods that are not expressly disclosed herein.

It is believed that the disclosure set forth above encompasses multiple distinct inventions with independent utility. While each of these inventions has been disclosed in its preferred form, the specific embodiments thereof as disclosed and illustrated herein are not to be considered in a limiting sense as numerous variations are possible. The subject matter of the inventions includes all novel and non-obvious combinations and subcombinations of the various elements, features, functions and/or properties disclosed herein. Similarly, when the disclosure or subsequently filed claims recite "a" or "a first" element or the equivalent thereof, such disclosure and/or claims should be understood to include incorporation of one or more such elements, neither requiring nor excluding two or more such elements.

The invention claimed is:

1. A garment configured to be worn by a wearer, the garment comprising:
   a garment base comprising an interior side and an exterior side, wherein the interior side faces the wearer when the garment is worn by the wearer, and wherein the exterior side faces outwardly away from the wearer when the garment is worn by the wearer;
   a fluid retention assembly coupled to the interior side of the garment base, wherein the garment base is continuous and underlies all of the fluid retention assembly, wherein the fluid retention assembly comprises:
      an assembly interior side that faces the wearer when the garment is worn by the wearer;
      an assembly exterior side that faces outwardly away from the wearer when the garment is worn by the wearer, wherein the assembly exterior side faces the interior side of the garment base;
      a first fluid-retention zone configured to absorb fluid excreted from the wearer when the garment is worn, wherein the first fluid-retention zone comprises a first absorbent layer;
      a second fluid-retention zone configured to absorb fluid excreted from the wearer when the garment is worn, wherein the second fluid-retention zone has a greater absorbency per unit area than the first fluid-retention zone, and wherein the second fluid-retention zone comprises the first absorbent layer and a second absorbent layer overlapped with the first absorbent layer; and
      a moisture-impermeable layer positioned with respect to the garment base such that the moisture-impermeable layer separates the interior side of the garment base from the first fluid-retention zone and from the second fluid-retention zone, such that the moisture-impermeable layer is configured to restrict fluid from exiting the fluid retention assembly to the exterior side of the garment base; and
   a bonded region comprising a plurality of adhesive bonds, wherein the plurality of adhesive bonds comprises an internal peripheral bond along a perimeter of the second absorbent layer, wherein the internal peripheral bond along the perimeter of the second absorbent layer bonds the second absorbent layer to a moisture-wicking layer of the fluid retention assembly, and wherein at least a portion of the perimeter of the second absorbent layer is not bonded to the first absorbent layer.

2. The garment according to claim 1, further comprising one or more additional fluid-retention zones comprising one or more additional absorbent layers, wherein each respective additional absorbent layer of the one or more additional absorbent layers overlaps a portion of a respective second absorbent layer.

3. The garment according to claim 1, wherein the internal peripheral bond along the perimeter of the second absorbent layer comprises a left lateral-edge portion and a right lateral-edge portion, and wherein the first absorbent layer and the second absorbent layer are not bonded together except along some or all of the left and right lateral-edge portions.

4. The garment according to claim 1, further comprising a bonded region comprising a plurality of adhesive bonds, wherein the plurality of adhesive bonds comprises an internal peripheral bond along a perimeter of the first absorbent layer, wherein the internal peripheral bond along the perimeter of the first absorbent layer bonds the first absorbent layer to the moisture-impermeable layer.

5. The garment according to claim 1, wherein the garment defines one or more garment apertures, wherein at least a portion of the first absorbent layer substantially follows a contour of at least one garment aperture of the one or more garment apertures, and wherein at least a portion of the second absorbent layer substantially follows the contour of the at least one garment aperture of the one or more garment apertures.

6. The garment according to claim 1, wherein the exterior side of the garment base is free from seams along an assembly perimeter of the fluid retention assembly.

7. The garment according to claim 6, wherein the first fluid-retention zone and the second fluid-retention zone are between a moisture-wicking layer of the fluid retention assembly and the moisture-impermeable layer.

8. The garment according to claim 7, wherein the fluid retention assembly comprises the moisture-wicking layer, wherein the moisture-wicking layer defines the assembly interior side of the fluid retention assembly, and wherein the moisture-wicking layer of the fluid retention assembly is configured to be positioned against the wearer when the garment is worn by the wearer.

9. The garment according to claim 1, wherein the garment comprises a plurality of fluid retention assemblies spaced apart from one another.

10. The garment according to claim 1, wherein the second fluid-retention zone comprises a plurality of second fluid-retention zones.

11. The garment according to claim 1, wherein the second fluid-retention zone extends superiorly to a lesser extent than does the first fluid-retention zone on an anterior side of the garment.

12. The garment according to claim 1, wherein the second fluid-retention zone extends superiorly to a lesser extent than does the first fluid-retention zone on a posterior side of the garment.

13. The garment according to claim 1, wherein the garment includes a waistband region, wherein the first fluid-retention zone extends to the waistband region on an anterior side of the garment, wherein the second fluid-retention zone does not extend to the waistband region on the anterior side of the garment, wherein the first fluid-retention zone does not extend to the waistband region on a posterior side of the garment, and wherein the second fluid-retention zone does not extend to the waistband region on the posterior side of the garment.

14. The garment according to claim 1, wherein the garment includes a waistband region, wherein the first fluid-retention zone does not extend to the waistband region on an anterior side of the garment, wherein the second fluid-retention zone does not extend to the waistband region on the anterior side of the garment, wherein the first fluid-retention zone extends to the waistband region on a posterior side of the garment, and wherein the second fluid-retention zone does not extend to the waistband region on the posterior side of the garment.

15. The garment according to claim 1, further comprising a bonded region comprising a plurality of adhesive bonds, wherein the plurality of adhesive bonds includes one or more assembly-base bonds, and wherein each assembly-base bond of the one or more assembly-base bonds operates to bond at least a portion of the fluid retention assembly to at least a portion of the garment base.

16. The garment according to claim 1, wherein the garment is a top, and wherein the garment is configured to be washed and re-worn numerous times.

17. A method of manufacturing the garment according to claim 1, the method comprising:
  forming the fluid retention assembly, wherein forming the fluid retention assembly comprises bonding the second absorbent layer to the first absorbent layer to form the second fluid-retention zone; and
  bonding, with a plurality of adhesive bonds, the fluid retention assembly to the garment base.

18. A garment configured to be worn by a wearer, the garment comprising:
  a bonded region;
  a garment base comprising an interior side and an exterior side, wherein the interior side faces the wearer when the garment is worn by the wearer, and wherein the exterior side faces outwardly away from the wearer when the garment is worn by the wearer; and
  a fluid retention assembly bonded to the interior side of the garment base within the bonded region via a plurality of adhesive bonds, wherein the garment base is continuous and underlies all of the fluid retention assembly, wherein the fluid retention assembly comprises:
    an assembly interior side that faces the wearer when the garment is worn by the wearer;
    an assembly exterior side that faces outwardly away from the wearer when the garment is worn by the wearer, wherein the assembly exterior side faces the interior side of the garment base;
    a first absorbent layer;
    a second absorbent layer overlapped with the first absorbent layer; and
    a moisture-impermeable layer positioned with respect to the garment base such that the moisture-impermeable layer separates the interior side of the garment base from the first absorbent layer, such that the moisture-impermeable layer is configured to restrict and/or at least substantially prevent fluid from exiting the fluid retention assembly to the exterior side of the garment base, and wherein the plurality of adhesive bonds comprises an internal peripheral bond along a perimeter of the second absorbent layer, wherein the internal peripheral bond along the perimeter of the second absorbent layer bonds the second absorbent layer to a moisture-wicking layer of the fluid retention assembly, and wherein at least a portion of the perimeter of the second absorbent layer is not bonded to the first absorbent layer.

19. A garment configured to be worn by a wearer, the garment comprising:
  a garment base comprising an interior side and an exterior side, wherein the interior side faces the wearer when the garment is worn by the wearer, and wherein the exterior side faces outwardly away from the wearer when the garment is worn by the wearer;
  a fluid retention assembly coupled to the interior side of the garment base, wherein the garment base is continuous and underlies all of the fluid retention assembly, wherein the fluid retention assembly comprises:
    an assembly interior side that faces the wearer when the garment is worn by the wearer;
    an assembly exterior side that faces outwardly away from the wearer when the garment is worn by the wearer, wherein the assembly exterior side faces the interior side of the garment base;
    a first fluid-retention zone configured to absorb fluid excreted from the wearer when the garment is worn, wherein the first fluid-retention zone comprises a first absorbent layer;
    a second fluid-retention zone configured to absorb fluid excreted from the wearer when the garment is worn, wherein the second fluid-retention zone has a greater absorbency per unit area than the first fluid-retention zone, and wherein the second fluid-retention zone comprises the first absorbent layer and a second absorbent layer overlapped with the first absorbent layer; and
    a moisture-impermeable layer positioned with respect to the garment base such that the moisture-impermeable layer separates the interior side of the garment base from the first fluid-retention zone and from the second fluid-retention zone, such that the moisture-impermeable layer is configured to restrict fluid from exiting the fluid retention assembly to the exterior side of the garment base; and
  a bonded region comprising a plurality of adhesive bonds, wherein the plurality of adhesive bonds comprises an internal peripheral bond along a perimeter of the first absorbent layer, wherein the internal peripheral bond along the perimeter of the first absorbent layer bonds the first absorbent layer to the moisture-impermeable layer.

20. The garment according to claim 19, wherein the garment defines one or more garment apertures, wherein at least a portion of the first absorbent layer substantially follows a contour of at least one garment aperture of the one or more garment apertures, and wherein at least a portion of the second absorbent layer substantially follows the contour of the at least one garment aperture of the one or more garment apertures.

21. The garment according to claim 19, wherein the exterior side of the garment base is free from seams along an assembly perimeter of the fluid retention assembly.

22. The garment according to claim 19, wherein, on an anterior side of the garment, the second fluid-retention zone extends superiorly to a lesser extent than the first fluid-retention zone.

23. The garment according to claim 19, wherein, on a posterior side of the garment, the second fluid-retention zone extends superiorly to a lesser extent than the first fluid-retention zone.

* * * * *